(12) United States Patent
Lapidus

(10) Patent No.: US 7,666,593 B2
(45) Date of Patent: Feb. 23, 2010

(54) SINGLE MOLECULE SEQUENCING OF CAPTURED NUCLEIC ACIDS

(75) Inventor: Stanley Lapidus, Bedford, NH (US)

(73) Assignee: Helicos Biosciences Corporation, Cambridge, MA (US)

( * ) Notice: Subject to any disclaimer, the term of this patent is extended or adjusted under 35 U.S.C. 154(b) by 124 days.

(21) Appl. No.: 11/213,621

(22) Filed: Aug. 26, 2005

(65) Prior Publication Data

US 2007/0048744 A1   Mar. 1, 2007

(51) Int. Cl.
C12Q 1/68   (2006.01)

(52) U.S. Cl. .......................................................... 435/6
(58) Field of Classification Search ........................ None
See application file for complete search history.

(56) References Cited

U.S. PATENT DOCUMENTS

| | | | |
|---|---|---|---|
| 3,996,345 A | 12/1976 | Ullman et al. |
| 4,119,368 A | 10/1978 | Yamazaki |
| 4,153,855 A | 5/1979 | Feingold |
| 4,344,064 A | 8/1982 | Bitler et al. |
| 4,351,760 A | 9/1982 | Khanna et al. |
| 4,683,195 A | 7/1987 | Mullis et al. |
| 4,683,202 A | 7/1987 | Mullis |
| 4,707,237 A | 11/1987 | Lepp et al. |
| 4,711,955 A | 12/1987 | Ward et al. |
| 4,725,677 A | 2/1988 | Koster et al. |
| 4,739,044 A | 4/1988 | Stabinsky |
| 4,757,141 A | 7/1988 | Fung et al. |
| 4,793,705 A | 12/1988 | Shera |
| 4,811,218 A | 3/1989 | Hunkapiller et al. |
| 4,863,849 A | 9/1989 | Melamede |
| 4,865,968 A | 9/1989 | Orgel et al. |
| 4,889,818 A | 12/1989 | Gelfand et al. |
| 4,942,124 A | 7/1990 | Church |
| 4,962,037 A | 10/1990 | Jett et al. |
| 4,971,903 A | 11/1990 | Hyman |
| 4,979,824 A | 12/1990 | Mathies et al. |
| 4,994,368 A | 2/1991 | Goodman et al. |
| 4,994,372 A | 2/1991 | Tabor et al. |
| 4,994,373 A | 2/1991 | Stavrianopoulos et al. |
| 5,085,562 A | 2/1992 | Van Lintel |
| 5,091,652 A | 2/1992 | Mathies et al. |
| 5,096,388 A | 3/1992 | Weinberg |
| 5,096,554 A | 3/1992 | Chin |
| 5,108,892 A | 4/1992 | Burke et al. |
| 5,112,736 A | 5/1992 | Caldwell et al. |
| RE34,069 E | 9/1992 | Koster et al. |
| 5,143,854 A | 9/1992 | Pirrung et al. |
| 5,167,784 A | 12/1992 | Noolandi |
| 5,171,132 A | 12/1992 | Miyazaki et al. |
| 5,198,540 A | 3/1993 | Koster |
| 5,209,834 A | 5/1993 | Shera |
| 5,224,843 A | 7/1993 | Van Lintel |
| 5,242,796 A | 9/1993 | Prober et al. |
| 5,242,797 A | 9/1993 | Hirschfeld |
| 5,258,506 A | 11/1993 | Urdea et al. |
| 5,259,737 A | 11/1993 | Kamisuki et al. |
| 5,260,433 A | 11/1993 | Engelhardt et al. |
| 5,265,327 A | 11/1993 | Faris et al. |
| 5,267,152 A | 11/1993 | Yang et al. |
| 5,302,509 A | 4/1994 | Cheeseman |
| 5,304,487 A | 4/1994 | Wilding et al. |
| 5,306,403 A | 4/1994 | Vo-Dinh |
| 5,336,062 A | 8/1994 | Richter |
| 5,360,523 A | 11/1994 | Middendorf et al. |
| 5,375,979 A | 12/1994 | Trah |
| 5,376,252 A | 12/1994 | Ekstrom et al. |
| 5,403,709 A | 4/1995 | Agrawal et al. |
| 5,405,747 A | 4/1995 | Jett et al. |
| 5,405,783 A | 4/1995 | Pirrung et al. |
| 5,409,811 A | 4/1995 | Tabor et al. |
| 5,424,186 A | 6/1995 | Fodor et al. |
| 5,436,149 A | 7/1995 | Barnes |
| 5,449,767 A | 9/1995 | Ward et al. |
| 5,476,928 A | 12/1995 | Ward et al. |
| 5,484,701 A | 1/1996 | Cocuzza et al. |
| 5,492,806 A | 2/1996 | Drmanac et al. |
| 5,514,256 A | 5/1996 | Douthart et al. |
| 5,518,900 A | 5/1996 | Nikiforov et al. |
| 5,525,464 A | 6/1996 | Drmanac et al. |
| 5,529,465 A | 6/1996 | Zengerle et al. |
| 5,534,125 A | 7/1996 | Middendorf et al. |
| 5,547,839 A | 8/1996 | Dower et al. |
| 5,547,859 A | 8/1996 | Goodman et al. |

(Continued)

FOREIGN PATENT DOCUMENTS

EP   0223618 A2   5/1987

(Continued)

OTHER PUBLICATIONS

International Search Report for corresponding International Application No. PCT/US2006/033214 (5 pages).

(Continued)

*Primary Examiner*—James Martinell
(74) *Attorney, Agent, or Firm*—Thomas Meyers; Adam Schoen; Brown Rudnick LLP

(57) ABSTRACT

The invention provides methods and devices for detecting, enumerating or identifying target nucleic acid molecules using immobilized capture probes and single molecule sequencing techniques.

12 Claims, No Drawings

U.S. PATENT DOCUMENTS

| | | |
|---|---|---|
| 5,556,790 A | 9/1996 | Pettit |
| 5,558,991 A | 9/1996 | Trainor |
| 5,599,695 A | 2/1997 | Pease et al. |
| 5,610,287 A | 3/1997 | Nikiforov et al. |
| 5,631,734 A | 5/1997 | Stern et al. |
| 5,632,957 A | 5/1997 | Heller et al. |
| 5,654,149 A | 8/1997 | Mendoza et al. |
| 5,659,171 A | 8/1997 | Young et al. |
| 5,670,346 A | 9/1997 | Reeve et al. |
| 5,674,716 A | 10/1997 | Tabor et al. |
| 5,675,155 A | 10/1997 | Pentoney, Jr. et al. |
| 5,688,648 A | 11/1997 | Mathies et al. |
| 5,695,940 A | 12/1997 | Drmanac et al. |
| 5,705,018 A | 1/1998 | Hartley |
| 5,707,506 A | 1/1998 | Douthart et al. |
| 5,710,628 A | 1/1998 | Waterhouse et al. |
| 5,712,476 A | 1/1998 | Renfrew et al. |
| 5,733,729 A | 3/1998 | Lipshutz et al. |
| 5,741,640 A | 4/1998 | Fuller |
| 5,741,644 A | 4/1998 | Kambara et al. |
| 5,744,305 A | 4/1998 | Fodor et al. |
| 5,744,312 A | 4/1998 | Mamone et al. |
| 5,750,341 A | 5/1998 | Macevicz |
| 5,753,788 A | 5/1998 | Fodor et al. |
| 5,755,943 A | 5/1998 | Middendorf et al. |
| 5,756,285 A | 5/1998 | Fuller |
| 5,759,014 A | 6/1998 | Van Lintel |
| 5,759,374 A | 6/1998 | Takahashi et al. |
| 5,762,876 A | 6/1998 | Lincoln et al. |
| 5,763,594 A | 6/1998 | Hiatt et al. |
| 5,776,767 A | 7/1998 | Stevens et al. |
| 5,776,782 A | 7/1998 | Tsuji |
| 5,789,168 A | 8/1998 | Leushner et al. |
| 5,795,722 A | 8/1998 | Lacroix et al. |
| 5,795,782 A | 8/1998 | Church et al. |
| 5,807,679 A | 9/1998 | Kamb |
| 5,808,045 A | 9/1998 | Hiatt et al. |
| 5,830,657 A | 11/1998 | Leushner et al. |
| 5,831,070 A | 11/1998 | Pease et al. |
| 5,832,165 A | 11/1998 | Reichert et al. |
| 5,834,758 A | 11/1998 | Trulson et al. |
| 5,836,750 A | 11/1998 | Cabuz |
| 5,837,832 A | 11/1998 | Chee et al. |
| 5,837,860 A | 11/1998 | Anderson et al. |
| 5,846,396 A | 12/1998 | Zanzucchi et al. |
| 5,846,727 A | 12/1998 | Soper et al. |
| 5,853,979 A | 12/1998 | Green et al. |
| 5,858,671 A | 1/1999 | Jones |
| 5,861,287 A | 1/1999 | Metzker et al. |
| 5,863,722 A | 1/1999 | Brenner |
| 5,872,244 A | 2/1999 | Hiatt et al. |
| 5,876,187 A | 3/1999 | Afromowitz et al. |
| 5,876,934 A | 3/1999 | Duthie et al. |
| 5,882,904 A | 3/1999 | Riedl et al. |
| 5,885,813 A | 3/1999 | Davis et al. |
| 5,889,165 A | 3/1999 | Fodor et al. |
| 5,902,723 A | 5/1999 | Dower et al. |
| 5,908,755 A | 6/1999 | Kumar et al. |
| 5,916,747 A | 6/1999 | Gilchrist et al. |
| 5,922,591 A | 7/1999 | Anderson et al. |
| 5,922,608 A | 7/1999 | Farnsworth et al. |
| 5,928,906 A | 7/1999 | Koster et al. |
| 5,928,919 A | 7/1999 | Reha-Krantz et al. |
| 5,945,283 A | 8/1999 | Kwok et al. |
| 5,945,284 A | 8/1999 | Livak et al. |
| 5,945,312 A | 8/1999 | Goodman et al. |
| 5,945,325 A | 8/1999 | Arnold et al. |
| 5,948,614 A | 9/1999 | Chatterjee |
| 5,952,174 A | 9/1999 | Nikiforov et al. |
| 5,954,932 A | 9/1999 | Takahashi et al. |
| 5,958,703 A | 9/1999 | Dower et al. |
| 5,959,781 A | 9/1999 | Kintz et al. |
| 5,959,837 A | 9/1999 | Yu |
| 5,965,446 A | 10/1999 | Ishikawa |
| 5,968,740 A | 10/1999 | Fodor et al. |
| 5,974,164 A | 10/1999 | Chee |
| 5,976,338 A | 11/1999 | Fujita et al. |
| 5,981,186 A | 11/1999 | Gabe et al. |
| 5,981,956 A | 11/1999 | Stern |
| 5,994,058 A | 11/1999 | Senapathy |
| 5,994,085 A | 11/1999 | Cantor |
| 6,002,471 A | 12/1999 | Quake |
| 6,005,663 A | 12/1999 | Waterhouse et al. |
| 6,007,309 A | 12/1999 | Hartley |
| 6,015,714 A | 1/2000 | Baldarelli et al. |
| 6,017,702 A | 1/2000 | Lee et al. |
| 6,018,041 A | 1/2000 | Drmanac et al. |
| 6,020,457 A | 2/2000 | Klimash et al. |
| 6,024,925 A | 2/2000 | Little et al. |
| 6,025,136 A | 2/2000 | Drmanac |
| 6,028,190 A | 2/2000 | Mathies et al. |
| 6,030,782 A | 2/2000 | Anderson et al. |
| 6,043,080 A | 3/2000 | Lipshutz et al. |
| 6,046,005 A | 4/2000 | Ju et al. |
| 6,049,380 A | 4/2000 | Goodwin et al. |
| 6,051,380 A | 4/2000 | Sosnowski et al. |
| 6,066,454 A | 5/2000 | Lipshutz et al. |
| 6,071,394 A | 6/2000 | Cheng et al. |
| 6,077,664 A | 6/2000 | Slater et al. |
| 6,077,674 A | 6/2000 | Schleifer et al. |
| 6,087,095 A | 7/2000 | Rosenthal et al. |
| 6,087,099 A | 7/2000 | Gupte et al. |
| 6,094,274 A | 7/2000 | Yokoi |
| 6,107,032 A | 8/2000 | Kilger et al. |
| 6,107,044 A | 8/2000 | Nikiforov |
| 6,107,061 A | 8/2000 | Johnson |
| 6,132,580 A | 10/2000 | Mathies et al. |
| 6,133,436 A | 10/2000 | Koster et al. |
| 6,136,212 A | 10/2000 | Mastrangelo et al. |
| 6,136,962 A | 10/2000 | Shi et al. |
| 6,140,053 A | 10/2000 | Koster |
| 6,140,494 A | 10/2000 | Hamilton et al. |
| 6,141,096 A | 10/2000 | Stern et al. |
| 6,143,151 A | 11/2000 | Middendorf et al. |
| 6,147,205 A | 11/2000 | McGall et al. |
| 6,156,501 A | 12/2000 | McGall et al. |
| 6,165,694 A | 12/2000 | Liu |
| 6,177,249 B1 | 1/2001 | Kwok et al. |
| 6,197,506 B1 | 3/2001 | Fodor et al. |
| 6,197,595 B1 | 3/2001 | Anderson et al. |
| 6,207,381 B1 | 3/2001 | Larsson et al. |
| 6,207,960 B1 | 3/2001 | Stern |
| 6,210,896 B1 | 4/2001 | Chan |
| 6,214,246 B1 | 4/2001 | Craighead |
| 6,214,987 B1 | 4/2001 | Hiatt et al. |
| 6,221,592 B1 | 4/2001 | Schwartz et al. |
| 6,221,654 B1 | 4/2001 | Quake et al. |
| 6,225,052 B1 | 5/2001 | Batz et al. |
| 6,225,062 B1 | 5/2001 | Dunn et al. |
| 6,225,092 B1 | 5/2001 | Kilger et al. |
| 6,225,109 B1 | 5/2001 | Juncosa et al. |
| 6,225,567 B1 | 5/2001 | Kester |
| 6,225,625 B1 | 5/2001 | Pirrung et al. |
| 6,228,593 B1 | 5/2001 | Lipshutz et al. |
| 6,232,075 B1 | 5/2001 | Williams |
| 6,232,103 B1 | 5/2001 | Short |
| 6,235,465 B1 | 5/2001 | Kolberg et al. |
| 6,235,473 B1 | 5/2001 | Friedman et al. |
| 6,242,180 B1 | 6/2001 | Chee |
| 6,242,528 B1 | 6/2001 | Clark et al. |
| 6,245,506 B1 | 6/2001 | Laugharn, Jr. et al. |
| 6,245,507 B1 | 6/2001 | Bogdanov |
| 6,245,518 B1 | 6/2001 | Baier |
| 6,251,610 B1 | 6/2001 | Gupte et al. |

| | | |
|---|---|---|
| 6,255,083 B1 | 7/2001 | Williams |
| 6,255,475 B1 | 7/2001 | Kwiatkowski |
| 6,258,533 B1 | 7/2001 | Jones |
| 6,261,775 B1 | 7/2001 | Bastian et al. |
| 6,261,776 B1 | 7/2001 | Pirrung et al. |
| 6,261,848 B1 | 7/2001 | Anderson et al. |
| 6,262,838 B1 | 7/2001 | Montagu |
| 6,263,286 B1 | 7/2001 | Gilmanshin et al. |
| 6,268,152 B1 | 7/2001 | Fodor et al. |
| 6,268,219 B1 | 7/2001 | Mcbride et al. |
| 6,269,846 B1 | 8/2001 | Overbeck et al. |
| 6,270,644 B1 | 8/2001 | Mathies et al. |
| 6,270,961 B1 | 8/2001 | Drmanac |
| 6,274,320 B1 | 8/2001 | Rothberg et al. |
| 6,274,351 B1 | 8/2001 | Peponnet |
| 6,277,604 B1 | 8/2001 | Peponnet |
| 6,280,954 B1 | 8/2001 | Ulfendahl |
| 6,284,460 B1 | 9/2001 | Fodor et al. |
| 6,287,821 B1 | 9/2001 | Shi et al. |
| 6,294,336 B1 | 9/2001 | Boyce-Jacino et al. |
| 6,294,337 B1 | 9/2001 | Hayashizaki |
| 6,306,607 B2 | 10/2001 | Williams |
| 6,309,601 B1 | 10/2001 | Juncosa et al. |
| 6,309,701 B1 | 10/2001 | Barbera-Guillem |
| 6,309,824 B1 | 10/2001 | Drmanac |
| 6,309,836 B1 | 10/2001 | Kwiatowski |
| 6,309,886 B1 | 10/2001 | Ambrose et al. |
| 6,310,189 B1 | 10/2001 | Fodor et al. |
| 6,312,893 B1 | 11/2001 | Van Ness et al. |
| 6,316,191 B1 | 11/2001 | Drmanac et al. |
| 6,322,968 B1 | 11/2001 | Head et al. |
| 6,331,439 B1 | 12/2001 | Cherukuri et al. |
| 6,333,183 B1 | 12/2001 | Evans et al. |
| 6,335,824 B1 | 1/2002 | Overbeck |
| 6,337,185 B1 | 1/2002 | Asp et al. |
| 6,337,188 B1 | 1/2002 | Head et al. |
| 6,342,326 B1 | 1/2002 | Milton |
| 6,344,325 B1 | 2/2002 | Quake et al. |
| 6,346,379 B1 | 2/2002 | Gelfand et al. |
| 6,346,413 B1 | 2/2002 | Fodor et al. |
| 6,355,420 B1 | 3/2002 | Chan |
| 6,355,432 B1 | 3/2002 | Fodor et al. |
| 6,361,671 B1 | 3/2002 | Mathies et al. |
| 6,361,937 B1 | 3/2002 | Stryer |
| 6,368,562 B1 | 4/2002 | Yao |
| 6,368,699 B1 | 4/2002 | Gilbert et al. |
| 6,383,749 B2 | 5/2002 | Bochkariov et al. |
| 6,387,626 B1 | 5/2002 | Shi et al. |
| 6,395,232 B1 | 5/2002 | McBride |
| 6,395,559 B1 | 5/2002 | Swenson |
| 6,397,150 B1 | 5/2002 | Izmailov |
| 6,399,364 B1 | 6/2002 | Reeve et al. |
| 6,401,267 B1 | 6/2002 | Drmanac |
| 6,403,311 B1 | 6/2002 | Chan |
| 6,403,315 B1 | 6/2002 | Drmanac |
| 6,403,317 B1 | 6/2002 | Anderson |
| 6,403,320 B1 | 6/2002 | Read et al. |
| 6,403,957 B1 | 6/2002 | Fodor et al. |
| 6,404,907 B1 | 6/2002 | Gilchrist et al. |
| 6,406,893 B1 | 6/2002 | Knapp et al. |
| 6,407,858 B1 | 6/2002 | Montagu |
| 6,408,878 B2 | 6/2002 | Unger et al. |
| 6,416,952 B1 | 7/2002 | Pirrung et al. |
| 6,420,169 B1 | 7/2002 | Read et al. |
| 6,423,273 B1 | 7/2002 | O'Mara |
| 6,432,634 B1 | 8/2002 | Digby et al. |
| 6,436,641 B1 | 8/2002 | Izmailov |
| 6,436,646 B1 | 8/2002 | Nikiforov |
| 6,440,664 B1 | 8/2002 | Digby et al. |
| 6,440,722 B1 | 8/2002 | Knapp et al. |
| 6,444,106 B1 | 9/2002 | Mcbride et al. |
| 6,444,173 B1 | 9/2002 | Sjursen et al. |
| 6,444,424 B1 | 9/2002 | Chatterjee et al. |
| 6,444,461 B1 | 9/2002 | Knapp et al. |
| 6,447,724 B1 | 9/2002 | Jensen et al. |
| 6,448,090 B1 | 9/2002 | McBride |
| 6,451,536 B1 | 9/2002 | Fodor et al. |
| 6,479,267 B1 | 11/2002 | Davis et al. |
| 6,485,690 B1 | 11/2002 | Pfost et al. |
| 6,485,909 B1 | 11/2002 | Hong et al. |
| 6,485,944 B1 | 11/2002 | Church et al. |
| 6,495,363 B2 | 12/2002 | Bogdanov |
| 6,506,560 B1 | 1/2003 | Hughes et al. |
| 6,511,803 B1 | 1/2003 | Church et al. |
| 6,514,706 B1 | 2/2003 | Von Kalle et al. |
| 6,521,428 B1 | 2/2003 | Senapathy |
| 6,524,829 B1 | 2/2003 | Seeger |
| 6,528,258 B1 | 3/2003 | Russell |
| 6,528,288 B1 | 3/2003 | Senapathy |
| 6,537,755 B1 | 3/2003 | Drmanac |
| 6,537,757 B1 | 3/2003 | Langmore et al. |
| 6,546,340 B2 | 4/2003 | Lipshutz et al. |
| 6,551,784 B2 | 4/2003 | Fodor et al. |
| 6,551,817 B2 | 4/2003 | Besemer et al. |
| 6,554,987 B1 | 4/2003 | Gilchrist et al. |
| 6,555,349 B1 | 4/2003 | O'Donnell |
| 6,558,945 B1 | 5/2003 | Kao |
| 6,562,566 B1 | 5/2003 | Hoheisel |
| 6,566,059 B1 | 5/2003 | Stanton, Jr. et al. |
| 6,566,515 B1 | 5/2003 | McGall et al. |
| 6,573,047 B1 | 6/2003 | Hung et al. |
| 6,573,374 B1 | 6/2003 | Muehleger et al. |
| 6,576,424 B2 | 6/2003 | Fodor et al. |
| 6,576,425 B2 | 6/2003 | McGall et al. |
| 6,579,704 B2 | 6/2003 | Short |
| 6,582,923 B2 | 6/2003 | Stanton, Jr. et al. |
| 6,585,939 B1 | 7/2003 | Dapprich |
| 6,607,888 B2 | 8/2003 | Schwartz et al. |
| 6,610,482 B1 | 8/2003 | Fodor et al. |
| 6,613,513 B1 | 9/2003 | Parco et al. |
| 6,623,928 B2 | 9/2003 | Van Ness et al. |
| 6,627,748 B1 | 9/2003 | Ju et al. |
| 6,632,655 B1 | 10/2003 | Mehta et al. |
| 6,642,001 B1 | 11/2003 | Bolk et al. |
| 6,664,079 B2 | 12/2003 | Ju et al. |
| 6,719,868 B1 | 4/2004 | Schueller et al. |
| 6,750,018 B2 | 6/2004 | Kambara et al. |
| 6,762,048 B2 | 7/2004 | Williams |
| 6,780,591 B2 | 8/2004 | Williams et al. |
| 6,783,938 B2 | 8/2004 | Nygren et al. |
| 6,787,308 B2 | 9/2004 | Balasubramanian et al. |
| 6,818,395 B1 | 11/2004 | Quake et al. |
| 6,908,736 B1 | 6/2005 | Densham |
| 6,911,345 B2 | 6/2005 | Quake et al. |
| 2001/0024790 A1 | 9/2001 | Kambara et al. |
| 2001/0044531 A1 | 11/2001 | McGall et al. |
| 2001/0046681 A1 | 11/2001 | Senapathy |
| 2002/0009744 A1 | 1/2002 | Bogdanov |
| 2002/0012910 A1 | 1/2002 | Weiss et al. |
| 2002/0015961 A1 | 2/2002 | Kwiatkowski |
| 2002/0025529 A1 | 2/2002 | Quake et al. |
| 2002/0032320 A1 | 3/2002 | Burgess et al. |
| 2002/0034792 A1 | 3/2002 | Kilger et al. |
| 2002/0039738 A1 | 4/2002 | Williams et al. |
| 2002/0042112 A1 | 4/2002 | Koster et al. |
| 2002/0045182 A1 | 4/2002 | Singh et al. |
| 2002/0051992 A1 | 5/2002 | Bridgham et al. |
| 2002/0053532 A1 | 5/2002 | Quake et al. |
| 2002/0061529 A1 | 5/2002 | Bridgham et al. |
| 2002/0072055 A1 | 6/2002 | Jones |
| 2002/0086318 A1 | 7/2002 | Manalis et al. |
| 2002/0102586 A1 | 8/2002 | Ju et al. |
| 2002/0102595 A1 | 8/2002 | Davis |
| 2002/0106673 A1 | 8/2002 | Drmanac et al. |
| 2002/0115076 A1 | 8/2002 | Williams |
| 2002/0115092 A1 | 8/2002 | Rebek, Jr. |

| | | | | | | |
|---|---|---|---|---|---|---|
| 2002/0119480 A1* | 8/2002 | Weir et al. ............... 435/6 | 2005/0147992 A1 | 7/2005 | Quake et al. |
| 2002/0119484 A1 | 8/2002 | Weidenhammer et al. | 2005/0170367 A1 | 8/2005 | Quake et al. |
| 2002/0123046 A1 | 9/2002 | Smith et al. | 2005/0239085 A1 | 10/2005 | Buzby et al. |
| 2002/0137046 A1 | 9/2002 | Koster | | | |
| 2002/0137052 A1 | 9/2002 | Bridgham et al. | FOREIGN PATENT DOCUMENTS | | |
| 2002/0137062 A1 | 9/2002 | Williams et al. | EP | 0579997 A1 | 1/1994 |
| 2002/0138205 A1 | 9/2002 | Miller et al. | EP | 0706004 A2 | 4/1996 |
| 2002/0142329 A1 | 10/2002 | Matray et al. | EP | 0779436 A2 | 6/1997 |
| 2002/0142333 A1 | 10/2002 | Gelfand et al. | EP | 0845603 A1 | 6/1998 |
| 2002/0146704 A1 | 10/2002 | Head et al. | EP | 0932700 B1 | 8/1999 |
| 2002/0146726 A1 | 10/2002 | Matray et al. | EP | 0946752 B1 | 10/1999 |
| 2002/0150903 A1 | 10/2002 | Koster | EP | 0955085 A2 | 11/1999 |
| 2002/0150938 A1 | 10/2002 | Kneipp et al. | EP | 0999055 A2 | 5/2000 |
| 2002/0164629 A1 | 11/2002 | Quake et al. | EP | 0706004 B1 | 8/2003 |
| 2002/0168642 A1 | 11/2002 | Drukier | GB | 2155152 A | 9/1985 |
| 2002/0168678 A1 | 11/2002 | Williams et al. | GB | 2308460 A | 6/1997 |
| 2002/0172948 A1 | 11/2002 | Perlin | GB | 2400518 A | 10/2004 |
| 2002/0177129 A1 | 11/2002 | Paabo et al. | SE | 9500589 | 2/1995 |
| 2002/0182601 A1 | 12/2002 | Sampson et al. | WO | 89/03432 A1 | 4/1989 |
| 2002/0192661 A1 | 12/2002 | Paabo et al. | WO | 89/09283 A1 | 10/1989 |
| 2002/0192662 A1 | 12/2002 | Boyce-Jacino et al. | WO | 90/13666 A1 | 11/1990 |
| 2002/0192691 A1 | 12/2002 | Drmanac | WO | 90/15070 A1 | 12/1990 |
| 2002/0197618 A1 | 12/2002 | Sampson | WO | 91/06678 A1 | 5/1991 |
| 2003/0003272 A1 | 1/2003 | Laguitton | WO | 92/10092 A1 | 6/1992 |
| 2003/0003498 A1 | 1/2003 | Digby et al. | WO | 92/10587 A1 | 6/1992 |
| 2003/0008285 A1 | 1/2003 | Fischer | WO | 93/05183 A1 | 3/1993 |
| 2003/0008413 A1 | 1/2003 | Kim et al. | WO | 93/06121 A1 | 4/1993 |
| 2003/0017461 A1 | 1/2003 | Singh et al. | WO | 93/21340 A1 | 10/1993 |
| 2003/0022207 A1 | 1/2003 | Balasubramanian et al. | WO | 95/12608 A1 | 5/1995 |
| 2003/0027140 A1 | 2/2003 | Ju et al. | WO | 95/27080 A1 | 10/1995 |
| 2003/0036080 A1 | 2/2003 | Jensen et al. | WO | 96/04547 A1 | 2/1996 |
| 2003/0044778 A1 | 3/2003 | Goelet et al. | WO | 96/12014 A1 | 4/1996 |
| 2003/0044779 A1 | 3/2003 | Goelet et al. | WO | 96/12039 A1 | 4/1996 |
| 2003/0044781 A1 | 3/2003 | Korlach et al. | WO | 96/27025 A1 | 9/1996 |
| 2003/0044816 A1 | 3/2003 | Denison et al. | WO | 97/02488 A1 | 1/1997 |
| 2003/0054181 A1 | 3/2003 | Swerdlow et al. | WO | 97/22076 A1 | 6/1997 |
| 2003/0054361 A1 | 3/2003 | Heller | WO | 97/23650 A2 | 7/1997 |
| 2003/0058440 A1 | 3/2003 | Scott et al. | WO | 97/37041 A2 | 10/1997 |
| 2003/0058799 A1 | 3/2003 | Yamakawa et al. | WO | 97/39150 A1 | 10/1997 |
| 2003/0059778 A1 | 3/2003 | Berlin et al. | WO | 97/40184 A1 | 10/1997 |
| 2003/0060431 A1 | 3/2003 | Simmonds et al. | WO | 97/41258 A1 | 11/1997 |
| 2003/0064366 A1 | 4/2003 | Hardin et al. | WO | 97/41259 A1 | 11/1997 |
| 2003/0064398 A1 | 4/2003 | Barnes | WO | 97/42348 A1 | 11/1997 |
| 2003/0064483 A1 | 4/2003 | Shaw et al. | WO | 98/00708 A1 | 1/1998 |
| 2003/0087237 A1 | 5/2003 | Hong et al. | WO | 98/02575 A1 | 1/1998 |
| 2003/0087300 A1 | 5/2003 | Knapp et al. | WO | 98/03684 A1 | 1/1998 |
| 2003/0092005 A1 | 5/2003 | Levene et al. | WO | 98/07069 A1 | 2/1998 |
| 2003/0092007 A1 | 5/2003 | Gibbs et al. | WO | 98/08978 A1 | 3/1998 |
| 2003/0096258 A1 | 5/2003 | Fu et al. | WO | 98/13523 A1 | 4/1998 |
| 2003/0100006 A1 | 5/2003 | Senapathy | WO | 98/20019 A1 | 5/1998 |
| 2003/0104437 A1 | 6/2003 | Barnes et al. | WO | 98/20020 A2 | 5/1998 |
| 2003/0104466 A1 | 6/2003 | Knapp et al. | WO | 98/20166 A2 | 5/1998 |
| 2003/0108867 A1 | 6/2003 | Chee et al. | WO | 98/21361 A1 | 5/1998 |
| 2003/0138809 A1 | 7/2003 | Williams et al. | WO | 98/27228 A1 | 6/1998 |
| 2003/0148344 A1 | 8/2003 | Rothberg et al. | WO | 98/28440 A1 | 7/1998 |
| 2003/0162213 A1 | 8/2003 | Fuller et al. | WO | 98/33939 A1 | 8/1998 |
| 2003/0186227 A1 | 10/2003 | Balasubramanian et al. | WO | 98/40520 A1 | 9/1998 |
| 2003/0186255 A1 | 10/2003 | Williams et al. | WO | 98/41650 A2 | 9/1998 |
| 2003/0190627 A1 | 10/2003 | Zhao et al. | WO | 98/41657 A1 | 9/1998 |
| 2003/0190647 A1 | 10/2003 | Odera | WO | 98/44152 A1 | 10/1998 |
| 2003/0190663 A1 | 10/2003 | Yang et al. | WO | 98/45481 A1 | 10/1998 |
| 2003/0194722 A1 | 10/2003 | Odedra et al. | WO | 98/53300 A2 | 11/1998 |
| 2003/0194740 A1 | 10/2003 | Williams | WO | 98/54669 A1 | 12/1998 |
| 2003/0215862 A1 | 11/2003 | Parce et al. | WO | 98/55593 A1 | 12/1998 |
| 2004/0009487 A1 | 1/2004 | Kadushin et al. | WO | 99/01768 A1 | 1/1999 |
| 2004/0014096 A1 | 1/2004 | Anderson et al. | WO | 99/05221 A1 | 2/1999 |
| 2004/0029115 A9 | 2/2004 | Dower et al. | WO | 99/05315 A2 | 2/1999 |
| 2004/0038206 A1 | 2/2004 | Zhang et al. | WO | 99/06422 A2 | 2/1999 |
| 2004/0054162 A1 | 3/2004 | Hanna | WO | 99/09616 A1 | 2/1999 |
| 2004/0106110 A1 | 6/2004 | Balasubramanian et al. | WO | 99/13109 A1 | 3/1999 |
| 2004/0126770 A1 | 7/2004 | Kumar et al. | WO | 99/13110 A1 | 3/1999 |
| 2005/0014175 A1 | 1/2005 | Quake | WO | 99/17093 A1 | 4/1999 |
| 2005/0100932 A1 | 5/2005 | Lapidus et al. | | | |

| | | | |
|---|---|---|---|
| WO | 99/19516 A1 | 4/1999 |
| WO | 99/24797 A1 | 5/1999 |
| WO | 99/27137 A1 | 6/1999 |
| WO | 99/31278 A1 | 6/1999 |
| WO | 99/37810 A1 | 7/1999 |
| WO | 99/39001 A2 | 8/1999 |
| WO | 99/40105 A2 | 8/1999 |
| WO | 99/40223 A1 | 8/1999 |
| WO | 99/41410 A1 | 8/1999 |
| WO | 99/44045 A1 | 9/1999 |
| WO | 99/45153 A2 | 9/1999 |
| WO | 99/47539 A1 | 9/1999 |
| WO | 99/47706 A1 | 9/1999 |
| WO | 99/53423 A1 | 10/1999 |
| WO | 99/57321 A1 | 11/1999 |
| WO | 99/61888 A2 | 12/1999 |
| WO | 99/64437 A1 | 12/1999 |
| WO | 99/64840 A1 | 12/1999 |
| WO | 99/65938 A2 | 12/1999 |
| WO | 99/66076 A1 | 12/1999 |
| WO | 99/66313 A1 | 12/1999 |
| WO | 00/00637 A2 | 1/2000 |
| WO | 00/06770 A1 | 2/2000 |
| WO | 00/09753 A1 | 2/2000 |
| WO | 00/11223 A1 | 3/2000 |
| WO | 00/17397 A1 | 3/2000 |
| WO | 00/26935 A2 | 5/2000 |
| WO | 00/30591 A1 | 6/2000 |
| WO | 00/34523 A1 | 6/2000 |
| WO | 00/37680 A1 | 6/2000 |
| WO | 00/40750 A1 | 7/2000 |
| WO | 00/40758 A2 | 7/2000 |
| WO | 00/42223 A1 | 7/2000 |
| WO | 00/43540 A1 | 7/2000 |
| WO | 00/43752 A1 | 7/2000 |
| WO | 00/50642 A1 | 8/2000 |
| WO | 00/53805 A1 | 9/2000 |
| WO | 00/53812 A2 | 9/2000 |
| WO | 00/56937 A2 | 9/2000 |
| WO | 00/58507 A1 | 10/2000 |
| WO | 00/58516 A2 | 10/2000 |
| WO | 00/68410 A1 | 11/2000 |
| WO | 00/70073 A1 | 11/2000 |
| WO | 00/71755 A2 | 11/2000 |
| WO | 00/79007 A1 | 12/2000 |
| WO | 01/01025 A3 | 1/2001 |
| WO | 01/16375 A2 | 3/2001 |
| WO | 01/23610 A2 | 4/2001 |
| WO | 01/24937 A2 | 4/2001 |
| WO | 01/25480 A2 | 4/2001 |
| WO | 01/31055 A2 | 5/2001 |
| WO | 01/32930 A1 | 5/2001 |
| WO | 01/38574 A1 | 5/2001 |
| WO | 01/48184 A2 | 5/2001 |
| WO | 01/42496 A2 | 6/2001 |
| WO | 01/57248 A2 | 8/2001 |
| WO | 01/57249 A1 | 8/2001 |
| WO | 01/61044 A1 | 8/2001 |
| WO | 01/64838 A2 | 9/2001 |
| WO | 01/75154 A2 | 10/2001 |
| WO | 01/79536 A1 | 10/2001 |
| WO | 01/85991 A2 | 11/2001 |
| WO | 01/92284 A1 | 12/2001 |
| WO | 01/96607 A2 | 12/2001 |
| WO | 02/00343 A1 | 1/2002 |
| WO | 02/02584 A1 | 1/2002 |
| WO | 02/02795 A2 | 1/2002 |
| WO | 02/02813 A2 | 1/2002 |
| WO | 02/03305 A2 | 1/2002 |
| WO | 02/04680 A2 | 1/2002 |
| WO | 02/20836 A2 | 3/2002 |
| WO | 02/20837 A2 | 3/2002 |
| WO | 02/27032 A1 | 4/2002 |
| WO | 02/29106 A2 | 4/2002 |
| WO | 02/30486 A3 | 4/2002 |
| WO | 02/35441 A2 | 5/2002 |
| WO | 02/36832 A2 | 5/2002 |
| WO | 02/44414 A2 | 6/2002 |
| WO | 02/061126 A2 | 8/2002 |
| WO | 02/061127 A2 | 8/2002 |
| WO | 02/072779 A2 | 9/2002 |
| WO | 02/072892 A1 | 9/2002 |
| WO | 02/077694 A1 | 10/2002 |
| WO | 02/079519 A1 | 10/2002 |
| WO | 02/088381 A2 | 11/2002 |
| WO | 02/088382 A2 | 11/2002 |
| WO | 02/097113 A2 | 12/2002 |
| WO | 02/099398 A1 | 12/2002 |
| WO | 03/002767 A1 | 1/2003 |
| WO | 03/016565 A2 | 2/2003 |
| WO | 03/020895 A2 | 3/2003 |
| WO | 03/020968 A2 | 3/2003 |
| WO | 03/021010 A2 | 3/2003 |
| WO | 03/031947 A2 | 4/2003 |
| WO | 03/044678 A1 | 5/2003 |
| WO | 03/048178 A2 | 6/2003 |
| WO | 03/062897 A1 | 7/2003 |
| WO | 03/106642 A2 | 12/2003 |
| WO | 2004/061119 A2 | 7/2004 |
| WO | 2004/074503 A2 | 9/2004 |
| WO | 2005/047523 A2 | 5/2005 |
| WO | WO-2005/040425 | 5/2005 |
| WO | 2005/080605 A2 | 9/2005 |

OTHER PUBLICATIONS

Written Opinion for corresponding International Application No. PCT/US2006/033214 (6 pages).

Adam et al., "Individual genomes targeted in sequencing revolution", *Nature*, vol. 411, p. 402 (May 2001).

Agrawal, S. et al., "Site Specific Functionalization of Oligodeoxynucleotides for Non-Radioactive Labelling", *Tetrahedron Letters*, vol. 31, No. 11, pp. 1543-1546 (1990).

Ambrose, W. et al., "Single Molecule Detection With Total Internal Reflection Excitation: Comparing Signal-to-Background and Total Signals in Different Geometries", *Cytometry*, vol. 36, pp. 224-231 (1999).

Amit, B. et al., "Photosensitive Protecting Groups of Amino Sugars and Their Use in Glycoside Synthesis . . . Derivatives", *I. Org. Chem.*, 39(2):192-6 (1974).

Arndt-Jovin, D. et al., "Immunofluorescence Localization of Z-DNA in Chromosomes: Quantitation by Scanning Microphotometry and Computer-assisted Image Analysis", 1. *The Journal of Cell Biology*, vol. 101, pp. 1422-1433, (Oct 1985).

Augustin, M.A., W. Ankenbauer, and B. Angerer, "Progress towards single-molecule sequencing: enzymatic synthesis of nucleotide-specifically labeled DNA." *Journal of Biotechnology*, 8(13): 289-301 (2001).

Axelrod, D., "Cell-Substrate Contacts Illuminated by Total Internal Reflection Fluorescence", 1. *The Journal of Cell Biology*, vol. 89, pp. 141-145, (Apr. 1981).

Axelrod, D. et al., "Total internal reflection fluorescent microscopy", *J Microscopy*, vol. 129, pp. 19-28, (1983).

Bai, X., et al., "Photocleavage of a 2-nitrobenzyl linker bridging a fluorophore to the 5' end of DNA" Proc Natl Acad Sci USA, 2003, vol. 100(2). p. 409-13.

Basche, T. et al., "Single Molecule Optical Detection, Imaging and Spectroscopy", Chs. 2 and 3, Weinheim:VCM, Germany (1997).

Beaucage, S. et al., "Advances in the Synthesis of Oligonucleotides by the Phosphoramidite Approach" Tetrahedron, 48:2223-2311 (1992).

Beese, L. et al., "Structure of DNA Polymerase I Klenow Fragment Bound to Duplex DNA", *Science*, 260:352-355 (1993).

Bennett et. al., "Solexa Sequencing chemistry can be applied to different platforms which will have common elements in detection and data processing", *Pharmacogenomics* 5(4), pp. 433-438, (2004).

Biesalski et al., "Preparation and Characterization of a Polyelectrolyte Monolayer Covalently Attached to a Planar Solid Surface", *Macromolecules III*, 32, 2309-2316. Article was published on the web Mar. 10, 1999.

Black, D.L., "Protein diversity from alternating splicing: A challenge for bioinformatics and post genome biology", *Cell*, 2000. 103(3): p. 367-370.

Blattner, F.R., et al., "The Complete genome sequence of *Escherichia coli* K-12.", *Science*, 277: 1453-74 (1997).

Boles et. al., "High-Resolution Mapping of Carcinogen Binding Sites on DNA", *Biochemistry*, 1986, 25, 3039-3043.

Brakmann, S. and P. Nieckchen, "The large fragment of *Escherichia coli* DNA polymerase I can synthesize DNA exclusively from fluorescently labeled nucleotides." *Chembiochem*, 2(10): 773-777 (2001).

Brakmann et. al, "Optimal Enzymes for Single-Molecule Sequencing", *Current Pharmaceutical Biotechnology*, 5, pp. 119-126(2004).

Braslavsky, I. et al., "Sequence Information can be obtained from single DNA molecules", *PNAS*, vol. 100, No. 7, pp. 3960-3964 (Apr. 2003).

Braslavsky, I. et al., "Objective-type dark-field illumination for scattering from microbeads", *Applied Optics*, vol. 40, No. 31, pp. 5650-5657, (Nov. 2001).

Braslavsky, I. et al., "Single Molecule Measurements of DNA Polymerase Activity: A Step Towards Single Molecule Sequencing", *Biophys. I. Abstracts*, p. 507A (2002).

Brechtel, R. et al., "Control of the electro osmotic flow by metal-salt-containing buffers", *J Chromatoraphy A*. vol. 716, pp. 97-105, (1995).

Bridgman, A. et al., "An improved method for the synthesis of mercurated dUTP. Enzymatic synthesis of Hg-labelled DNA of high molecular weight suitable for use in an image based DNA sequencing strategy", *DNA Seq.*, vol. 6, No. 4, pp. 199-209 (1996).

Bruggert, J. et al., "Microfabricated tools for nanoscience", *J. Micromech. Microeng.*, 3, pp. 161-167 (1993).

Bryzek, J. etal., "Micromachines on the march", *IEEE Spectrum*, vol. 31, No. 5, pp. 20-31, (1994).

Buchaillot, L. et al., "Silicon Nitride Thin Films Young's Modulus Determination by an Optical Non Destructive Method", *Jpn. J. Appl. Phys.*, vol. 36, pp. L794-L797, (Jun. 1997).

Burghardt, T. et al., "Total Internal Reflection Fluorescence Study of Energy Transfer in Surface-Adsorbed and Dissolved Bovine Serum Albumin", *Biochemistry*, vol. 22, pp. 979-985 (1983).

Burghardt, et al., "Total Internal Reflection/Fluorescence Photobleaching Recovery Study of Serum Albumin Adsorption Dynamics", *Biophys. Journal*, vol. 33, pp. 455-468 (Mar. 1981).

Butler, D. et al., "Draft data leave geneticists with a mountain still to climb", *Nature*, vol. 405, Issue 6782, pp. 984-985 (May 2000).

Canard, B., B. Cardona, and R.S. Sarfati, "Catalytic editing properties of DNA polymerases," *Proc Natl Acad Sci USA*, 92(24): p. 10859-63 (1995).

Canard, et al., "DNA polymerase fluorescent substrates with reversible 3'-tags", *Gene*, 148(1): 1-6 (1994).

Cheng et al , "High-speed DNA sequence analysis," *Prog. in Biochem. and Biophys.*, vol. 22, pp. 223-227 (1995), Abstract only.

Chicurel, M., "Faster, better, cheaper genotyping", *Nature*. vol. 412, Issue 6847, pp. 580-582, (Aug. 2001).

Chidgeavadze et al., 2',3'-Dideoxy-3' aminonucleoside 5'-triphosphates are the terminators of DNA synthesis catalyzed by DNA polymerases, *Nuc. Acids Res.*, 12(3):1671-1686 (1984).

Chidgeavadze, Z. et al., "3'-Fluro-2',3'-dideoxyribonucleoside 5'-triphosphates: terminators of DNA synthesis", *FEBS Letters*,183(2):275-278 (1985).

Chiu, D. et al., "Patterned deposition of cells and proteins onto surfaces by using three-dimensional microfluidic systems," *PNAS*. vol. 97, No. 6, pp. 2408-2413 (2000).

Chou et al., "A microfabricated device for sizing and sorting DNA molecules", Applied Sciences, Biophysics: Proc. Natl. Acad. Sci. USA 96, pp. 11-13 (1999).

Chou et al., "A Microfabricated Rotary Pump", Biomedical Microdevices. vol. 3: p. 323-330 (2001).

Close, D. et al., "Ultraviolet Photobleaching of Free Radicals Created in γ-Irradiated Amino Acids", *Radiation Research*, vol. 53, pp. 349-357(1973).

Cooper, J. et al., "Analysis of Fluorescence Energy Transfer in Duplex and Branched DNA Molecules", *Biochemistry*, vol. 29, pp. 9261-9268 (1990).

Crocker, J.C. and D.G. Grier, "Methods of digital video microscopy for colloidal studies." *Journal of Colloid and Interface Science*, 179(1): p. 298-310 (1996).

Dapprich, J., "Single-molecule DNA digestion by lambda-exonuclease." *Cytometry*, 36(3): p. 163-168 (1999).

Debenham, J.S., et al., "Two New Orthogonal Amine-Protecting Groups that can be Cleaved under Mild or Neutral Conditions." *Journal of the American Chemical Society*, 117(11): p. 3302-3 (1995).

Decher, G. et al. "Buildup of ultrathin multiplayer films by a self-assembly process: III. Consecutively alternating absorption of anionic and cationic polyelectrolytes on charged surfaces", *Thin Solid Films*, 210:831-835 (1992).

Decher G.;et al., "Fuzzy nanoassemblies : Toward layered polymeric multicomposites." *Science*, 277(5330): p. 1232-1237 (1997).

Delamarche, E. et al., "Patterned Delivery of Immunoglobulins to Surfaces Using Microfluidic Networks", *Science* 276:779-781 (1997).

Dickson et al., "Simultaneous Imaging of Individual Molecules aligned both parallel and perpendicular to the optic axis", *The American Physical Society*, vol. 81, No. 24, pp. 5322-5325 (1998).

Doktycz, M. et al., "Genosensors and Model Hybridization Studies", *Automation Technologies for Genome Characterization*, Ch. 10 T. Beugelsdijk (Ed), John Wiley & Sons, Inc., pp. 205-225 (1997).

Doublie, S. et al., "Crystal structure of a bacteriophage T7 DNA replication complex at 2.2 A resolution", *Nature*, vol. 391, pp. 251-258 (Jan. 1998).

Driscoll et al., "Atomic-Scale Imaging of DNA Using Scanning Tunneling Microscopy." *Nature*, 346(6281): p. 294-296 (1990).

Drmanac, R. et al., "Sequencing by hybridization: Towards an automated sequencing of one million M13 clones arrayed on membranes", *Electrophoresis*, 13:566-573 (1992).

Duffy et al., "Patterning Electroluminescence Materials with Feature Sizes as Small as 5 um Using Elastomeric Membrains as Masks for Dry Lift-Off," *Advanced Materials* vol. 11, No. 7, pp. 546-552 (1999).

Duffy et al., "Rapid prototyping of microfluidic switches in poly(dimethyl siloxane) and their acuation by electroosmotic flow," *J. Micromech. Microeng.*, vol. 9, pp. 211-217 (1999).

Duffy et al., "Rapid Prototyping of Microfluidic Systems in Poly(dimethylsiloxane)", *Analytical Chemistry*, vol. 70, No. 23, pp. 4974-4984 (1998).

Effenhauser et al., "Integrated capillary electrophoresis on Flexible silicone microdevices: Analysis of DNA restriction fragments and detection of single DNA molecules on microchips," *Anal. Chem.*, vol. 69, pp. 3451-3457 (1997).

Effenhauser et al., "Integrated chip-based capillary electrophoresis," *Electrophoresis*, vol, 18, pp. 2203-2213 (1997).

Eigen, M. et al., "Sorting single molecules: Application to diagnostics and evolutionary biotechnology", *PNAS*, vol. 91, pp. 5740-5747, (Jun. 1994).

Evangelista, R.A., et al. "Characterization of fluorescent nucleoside triphosphates by capillary electrophoresis with laser-induced fluorescence detection: action of alkaline phosphatase and DNA polymerase." *Analytical Biochemistry*, 235(1): p. 89-97 (1996).

Fahrenberg et al., "A microvalve system fabricated by thermoplastic molding," J. Micromech. Microeng., vol. 5, pp. 169-171(1995).

Ferguson, et al., "A fiber-optic DNA biosensor microarray for the analysis of gene expression," *Nature Biotechnology*, vol. 14, pp. 1681-1684 (1996).

Forster, T., "Delocalized Excitation and Excitation Transfer", Modem Quantum Chem., *Istanbul Lectures*, Part TII, pp. 93-137, Academic Press, New York (1965).

Fritz, I. et al., "Electronic detection of DNA by its intrinsic molecular charge", PNAS, vol. 99, No. 22, pp. 14142-14146 (Oct. 2002).

Fu et al., "A microfabricated fluorescence-activated cell sorter," *Nature Biotechnology*, vol. 17, pp. 1109-1111 (1999).

Fu e al., "An integrated microfabricated cell sorter", *Analytical Chemistry*, 74(11): pp. 2451-2457 (2002).

Funatsu, T. et al., "Imaging of single fluorescent molecules and individual ATP turnovers by single myosin molecules in aqueous solution", *Nature*, vol. 374, pp. 555-559 (Apr. 1995).

Garcia, A., "Determination of Ion Penneability by Fluorescence Quenching", *Meth. in Enzymology*. 207:501-511 (1992).

Gardner, A., et al., "Acyclic and dideoxy terminator preferences denote divergent sugar recognition by archaeon and *Taq* DNA polymerases", *Nucleic Acids Research*, vol. 30, No. 2, pp. 605-613 (2002).

Gardner et al., "Comparative kinetics of nucleotide analog incorporation by Vent DNA polymerase," *J. Biol. Chem.*, 279, No. 12, p. 11834-11842 (2004).

Giller et al., "Incorporation of reporter molecule-labeled nucleotides by DNA polymerases. I. Chemical synthesis of various reporter group-labeled 2'deoxyribonucleoside-5'-triphosphates," *Nucleic Acids Res.*, 31, No. 10, p. 2630-2635 (2003).

Giusti, W. et al., "Synthesis and Characterization of 5' -Fluorescent-dye-labeled Oligonucleotides", *PCR Methods and Applications*. 2:223-227 (1993).

Goll et al., "Microvalves with bistable buckled polymer diaphragms," *J. Micromech. Microeng.*, vol. 6., pp. 77-79 (1996).

Goodwin, P.M., et al., "Application of single molecule detection to DNA sequencing." *Nucleosides & Nucleotides*, 16(5-6): p. 543-550 (1997).

Gravesen et al., "Microfluidics—a review", *J. Micromech. Microeng.*, vol. 3, pp. 168-182 (1993).

Greene, T.W. and P.G.M. Wuts, "Protective Groups in Organic Synthesis." John Wiley & Sons, Inc.: New York, 1999 3rd Ed. pp. xi-xii only (Table of Contents).

Gueroui, Z., et al., "Observation by fluorescence microscopy of transcription on single combed DNA," *PNAS*, 99(9): p. 6005-6010 (2002).

Guilbault, G., "Practical Fluorescence—Theory, Methods and Techniques," Chapters 1 and 3, and pp. 521-524, Marcel Dekker, Inc., New York (1973).

Guillier, F., D. Orain, and M. Bradley, "Linkers and Cleavage Strategies in Solid-Phase Organic Synthesis and Combinatorial Chemistry." Chemical Reviews, 100(6): p. 2091-2157 (2000).

Gupta, K.C., et al., "A general method for the synthesis of 3'-sulfhydryl and phosphate group containing oligonucleotides", *Nucleic Acids Res.*, 1901:3019-25 (1991).

Gyllenstein, U. et al., "Generation of single-stranded DNA by the polymerase chain reaction and its application to direct sequencing of the *HLA-DQA* locus", *PNAS*, 85:7652-56 (1988).

Ha, "Single molecule dynamics studied by polarization modulation," Phys. Rev. Lett., 77, No. 19, 3979-3982 (1996).

Ha, "Single molecule spectroscopy with automated positioning," Appl. Phys. Lett. 70, No. 6, 782-784 (1997).

Ha, "Single-molecule fluorescence methods for the study of nucleic acids," Current Opinion in Struct Bio, 11, 287-292 (2001).

Ha et al., "Single-molecule fluorescence spectroscopy of enzyme conformational dynamics and cleavage mechanism," *PNAS*, 96(3): p. 893-898 (1999).

Ha, T., "Single-molecule fluorescence resonance energy transfer," *Methods*, 25(1): p. 78-86 (2001).

Hanna, M. et al., "Synthesis and characterization of a new photocrosslinking CTP analog and its use in photoaffmity labeling *E. coli* and T7 RNA Polymerases", *Nucleic Acids Res.*, 21(9):2073-2079 (1993).

Hansen, C.J., et al., "A robust and scalable microfluidic metering method that allows Protein crystal growth by free interface diffusion". Proc Natl Acad Sci U S A, 99(26): p. 16531-6 (2002).

Harding et al., "Single-molecule detection as an approach to rapid DNA sequencing," Trends in Biotechnology, vol. 10, 3 pages, (1992).

Harris, J.M., "Introduction to Biochemical and biomedical applications of poly(ethylene glycol)." Poly(ethylene glycol) Chemistry, Harris, J. M., Ed.; Plenum Press: New York, pp. 1-14 (1992).

Harrison et al., "Micromachining a miniaturized capillary electrophoresis-based chemical analysis system on a chip," Science, vol. 261, pp. 895-897 (1993).

Harrison, D., et al., "Towards miniaturized electrophoresis and chemical analysis systems on silicon: an alternative to chemical sensors", *Sensors and Actuators B*, 10, pp. 107-116 (1993).

Hasan, A. et al., "Photolabile Protecting Groups for Nucleosides: Synthesis and Photodeprotection Rates", *Tetrahedron*, 53(12):4247-4264 (1997).

Hornbeck, L. et al., "Bistable Defonnable Mirror Device", 1988 Techllical Digest Series, vol. 8, Optical Society of America, pp. 107-110, (Jun. 1988).

Hosokawa et al., "Handling of Picoliter liquid samples in a poly(dimethylsiloxane)-based microfluidic device," Anal. Chem., vol. 71, No. 20, pp. 4781-4785 (1999).

Houseal, T. et al., "Real-time imaging of single DNA molecules with fluorescence microscopy", *Biophys. I.*, vol. 56, pp. 507-516 (Sep. 1989).

Howorka, et al., "Sequence-specific detection of individual DNA strands using engineered nanopores." Nature Biotechnology, 19(7): p. 636-639 (2001).

Hubner et al., "Direct observation of the triplet lifetime quenching of single dye molecules by molecular oxygen," J. Chem. Physics, 115, No. 21, p. 9619-9622 (2001).

Hultman, T. et al., "Bidirectional Solid-Phase Sequencing of In Vitro-Amplified Plasmid DNA", *BioTechniques*, vol. 10, No. 1, pp. 84-93 (1991).

Hyman, E., "A New Method of Sequencing DNA", *Anal. Biochem.*, 174:423-436 (1988).

Ikuta et al., "Three dimensional micro integrated fluid systems (MIFS) fabricated by stereo lithography", *IEEE Kyushu Institute of Technology*, pp. 1-6, (1994).

Ishii et al., "Fluorescence resonance energy transfer between single fluorophores attached to a coiled-coil protein in aqueous solution," Chemical Physics, 247, 163-173 (1999).

Ishijima, A. et al., "Simultaneous Observation of Individual ATPase and Mechanical Events by a Single Myosin Molecule during Interaction with Actin", *Cell*, vol. 92, pp. 161-171, (Jan. 1998).

Ishikawa, M. et al., "Single-Molecule Detection by Laser-Induced Fluorescence Technique with a Position-Sensitive Photon-Counting Apparatus", *Appl. Phys.*, vol. 33, Part 1, No. 3A, pp. 1571-1576 (1994).

Jacobs et al., "Combinatorial chemistry—applications of light-directed chemical synthesis", *TIBTech*, vol. 12, pp. 19-26 (Jan. 1994).

Jacobson, K. et al., "International Workshop on the application of fluorescence photobleaching techniques to problems in cell biology", Workshop Summary, Federation Proceedings, vol. 42, pp. 72-79 (1983).

Jacobson, et al., "High-speed separations on a microchip," Anal. Chem., vol. 66, No. 7, pp. 1114-1118 (1994).

Jacobson, et al., Microfluidic devices for electrokinetically driven parallel and serial mixing, Anal. Chem., vol. 71, No. 20, pp. 4455-4459 (1999).

Jett, J. et al., "High-Speed DNA Sequencing: An Approach Based Upon Fluorescence Detection of Single Molecules", *J. Biomolecular Structure & Dynamics*, vol. 7, No. 2, pp. 301-309, (1989).

Johnston, R. et al., "Autoradiography using storage phosphor technology", *Electrophoresis*, 11 :355-360 (1990).

Jongeneel, C.V., et al., "Comprehensive sampling of gene expression in human cell lines with massively parallel signature sequencing". Proc Natl Acad Sci U S A, 100(8): pp. 4702-4705 (2005).

Joos, B. et al., "Covalent Attachment of Hybridizable Oligonucleotides to Glass Supports", *Anal. Biochem.* 247(1):96-101 (1997).

Kambara, H. et al., "Optimization of Parameters in a DNA Sequenator using Fluorescence Detection", *Biotechnology*, vol. 6, pp. 816-821 (1988).

Kartalov, Emil P., et al., "Microfluidic device reads up to four consecutive base pairs in DNA sequencing-by-synthesis", *Nucleic Acids Research*, vol. 32, No. 9, pp. 2873-2879 (2004).

Kartalov et al., "Single-Molecule Detection and DNA Sequencing-by-Synthesis," in Partial Fulfillment of the Requirements for the Degree of Doctor Philosophy, California Institute of technology, pp. 1-160 (2004).

Kartalov et al., "Poly-Electrolyte Surface-Chemistry Platform for Fluorescence Studies of DNA on Glass", http://www.ugcs.caltech.edu/~kartalov/PEM_6.pdf, pp. 1-7, last modified Jun. 7, 2002.

Kawai et al., "A simple method of detecting amplified DNA with immobilized probes on microtiter wells", Analytical Biochemistry, 209:63-69 (1993).

Kelso et al., "Single-cell analysis by RT-PCR reveals differential expression of multiple type 1 and 2 cytokine genes among cells within polarized CD4+ T cell populations," International Immunology, 11, No. 4, 617-621 (1999).

Kenis et al., "Microfabrication inside capillaries using multiphase laminar flow patterning," Science, vol. 285, pp. 83-85 (1999).

Kenney, et al., "Mutation Typing Using Electrophoresis and Gel-Immobilized Acrydite™ Probes," BioTechniques, vol. 25, No. 3, pp. 516-521, (1998).

Khandjian, E., "UV cross linking of RNA to nylon membrane enhances hybridization signals", Mole. Bio, Rep. 11: 107-115 (1986).

Khrapko, K. et al., "A method for DNA sequencing by hybridization with oligonucleotide matrix", DNA Sequence-J. DNA Sequencing and Mapping, vol. 1, pp. 375-388 (1991).

Kiefer, J. et al., "Crystal structure of a thermostable Bacillus DNA polymerase I large fragment at 2.1 A resolution", Structure, 5:95-108 (1997).

Kim, Y. et al., "Crystal structure of Thermus aquaticus DNA polymerase", Nature, 376:612-616 (1995).

Kirkland, T.A., D.M. Lynn, and R.H. Grubbs, "Ring-Closing Metathesis in Methanol and Water." Journal of Organic Chemistry, 63(26): p. 9904-9909 (1998).

Knerr, L. and R.R. Schmidt, "Application of a ring-closing-metathesis-based linker to the solid phase synthesis of oligosaccharides" Synlett, 11: p. 1802-1804(1999).

Kopp, et al., "Chemical Amplification: Continuous-Flow PCR on a Chip", Science, vol. 280, pp. 1046-1048 (May 1998).

Korolev, S. et al., "Crystal structure of the large fragment of Thermus aquaticus DNA polymerase I at 2.5 A resolution: Structural basis for thermo stability", PNAS, 92:9264-9268 (1995).

Kovacs et al., "Simple synthesis of 5-vinyl-and 5-ethynyl-2' deoxyuridine 5'-triphosphates", Tetrahedron Letters, 29(36): p. 4525-8 (1988).

Kricka et al., "Labels, Labeling, Analytical Strategies, and Applications." Ch. 1 and Table Ix, Academic Press, New York, pp. 3-40, (1995).

Krider, E. et al., "2'-Modified Nucleosides for Site-Specific Labeling of Oligonucleotides", Bioconjugate Chem., vol. 13, No. 1, pp. 155-162 (2002).

Kuhn, L. et al., "Silicon Charge Electrode Array for Ink Jet Printing", IEEE Trans. On Electron Dev., vol. ED-25, No. 10, pp. 1257-1260 (Oct. 1978).

Lacoste, T. et al., "Ultrahigh-resolution multicolor colocalization of single fluorescent probes", PNAS, 97(17):9461-6 (2000).

Lander, E.S., et al., "Initial sequencing and analysis of the human genome." Nature, 409(6822): p. 860-921 (2001).

Lazowski, K. et al., "Highly Sensitive Detection of Hybridization of Oligonucleotides to Specific Sequences of Nucleic Acids by Application of Fluorescence Resonance Energy Transfer", Antisense and Nucleic Acid Drug Dev., vol. 10, pp. 97-103 (2000).

Lee, "Enhancing the catalytic repertoire of nucleic acids: a systematic study of linker length and rigidity," Nucleic Acids Res., 29, No. 7, Apr. 1, 1565-1573 (2001).

Lee, Y. et al., "Laser-Induced Fluorescence Detection of a Single Molecule in a Capillary", Anal. Chem., vol. 66, pp. 4142-4149 (1994).

Levene, M. et al., "Zero-Mode Waveguides for Single-Molecule Analysis at High Concentrations", Science, 299:682-686 (Jan. 2003).

Levsky et al., "Single-cell gene expression profiling," Science, 297, 836-840 (2002).

Li, H. et al., "Ultrasensitive Coincidence Fluorescence Detection of Single DNA Molecules", Anal. Chem., 75:1664-1670 (2003).

Li, Y. et al., "Design, Synthesis, and Spectroscopic Properties of Peptide-Bridged Fluorescence Energy-Transfer Cassettes", Bioconjuate Chem., 10:241-245 (1999).

Li, Y. et al., "Structural Studies of the Klentaql DNA Polymerase", Current Organic Chem., 5:871-883 (2001).

Li, Z. et al., "A photocleavable fluorescent nucleotide for DNA sequencing and analysis", PNAS, vol. 100, No. 2, pp. 414-419 (2003).

Lin, L. et al., "Free-Space Micromachined Optical Switches for Optical Networking", IEEE J. of Selected Topics in Quanturn Electronics, vol. 5, No. 1, pp. 4-9 (Jan. 1999).

Liu, J., M.. Enzelberger, and S. Quake, "A nanoliter rotary device for polymerase chain reaction" Electrophoresis, 23(10): p. 1531-6 (2000).

Lodder, M., et al., "Misacylated Transfer RNAs Having a Chemically Removable Protecting Group." Journal of Organic Chemistry, 63(3): p. 794-803 (1998).

Loh, E. et al., "Polymerase Chain Reaction with Single-Sided Specificity: Analysis of T Cell Receptor D Chain", Science 243:217-220 (1989).

Lok, Corie, "Deciphering DNA, Top Speed—Helicos BioSciences aims to expedite sequencing, enable genomic medicine," Technology Review, pp. 27-28 (May 2005).

Lopez, G. et al., "Fabrication and Imaging of Two-Dimensional Patterns of Proteins Adsorbed on Self-Assembled Monolayers by Scanning Electron Microscopy", J. Amer. Chem. Soc., 115:10774-81 (1993).

Lotters et al., "The mechanical properties of the rubber elastic polymer polydimethylsiloxane for sensor applications," J. Micromech. Microeng., vol. 7, pp. 145-147 (1997).

Lucy et al., "Characterization of the cationic surfactant induced reversal of electroosmotic flow in capillary electrophoresis," Anal. Chem., vol. 68, pp. 300-305 (1996).

Ludwig, J and F. Eckstein, "Rapid and Efficient Synthesis of Nucleoside 5'- 0-(1-Thiotriphosphates), 5'-triphosphates and 2',3'-Cyclophosphorothioates Using 2-Chloro-4$H$-1,3,2-benzodioxaphosphorin-4-one."Journal of Organic Chemistry, 54(3): p. 631-635 (1989).

Lvov, Yu. et al., "Assembly of Thin Films by Means of Successive Deposition of Alternate Layers of DNA and Poly(allylamine)", American Chemical Society, Macromolecules, 26, pp. 5396-5399, (1993).

Macklin, J. et al., "Imaging and Time-Resolved Spectroscopy of Single Molecules at an Interface", Science, vol. 272, No. 5259, pp. 255-258 (Apr. 1996).

Maier, B., D. Bensimon, and V. Croquette, "Replication by a single DNA polymerase of a stretched single-stranded DNA." Proceedings of the National Academy of Sciences of the United States of America, 97(22): p. 12002-12007 (2000).

Marriott, G. et al., "Time resolved imaging microscopy—Phosphorescence and delayed fluorescence imaging", Biophys. J., vol. 60, pp. 1374-1387 (Dec. 1991).

Marziali, A. and M. Akeson, "New DNA sequencing methods." Annual Review of Biomedical Engineering, 3: p. 195-223(2001).

Mastrangelo, C. et al., "Vacuum-Sealed Silicon Micromachined Incandescent Light Source", IDEM, 89:503-506 (1989).

Meiners, J.C. and S.R. Quake, "Femonewton force spectroscopy of single extended DNA molecules." Phys Rev Lett, 84(21): p. 5014-7 (2000).

Meldrum, Kevin, "Microfluidics-based products for nucleic acid analysis", http://www.americanlaboratory.com/articles/al/a9909mel.pdf, 2 pages (Sep. 1999).

Meller, A., et al., "Rapid nanopore discrimination between single polynucleotide molecules." PNAS, 97(3): p. 1079-1084 (2000).

Mertz, J. et al., "Single-molecule detection by two-photon-excited fluorescence", Optics Letters, vol. 20, No. 24, pp. 2532-2534 (Dec. 1995).

Metzker et al., "Elimination of residual natural nucleotides from 3'-O-modified-dNTP syntheses by enzymatic mop-up," BioTechniques, 25, 814-817 (1998).

Metzker, M.L., et al., "Termination of DNA synthesis by novel 3'-modified-deoxyribonucleoside 5'-triphosphates." Nucleic Acids Res, 22(20): p. 4259-4267 (1994).

Mitra, Robi, et al., "Fluorescent in situ sequencing on polymerase colonies", Analytical Biochemistry, 320, pp. 55-65 (2003).

Moe et al., Rapid Detection of Clinically Relevant Bacteria in Platelets Using the Hybriscan Baceterial Detection system, Journal of the American Society of Hematology, 96, No. 11, 4155 (2000).

Moore, P., "To affinity and beyond", *Nature*, vol. 426, No. 6967, pp. 725-731, (2003).

Muller et al., "Surface-micromachined microoptical elements and systems," IEEE vol. 86, No. 8, pp. 1705-1720 (1998).

Nelson, P. et al., "Bifunctional oligonucleotide probes synthesized using a novel CPG support are able to detect single base pair mutations", *NAR*, 17(18):7187-7194 (1989).

Nie, S. et al., "Probing Individual Molecules with Confocal Fluorescence Microscopy", *Science*, vol. 266, No. 5187, pp. 1018-1021 (Nov. 1994).

Nyren, P. et al., "Solid Phase DNA Minisequencing by an Enzymatic Luminometric Inorganic Pyrophosphate Detection Assay", *Anal. Biochem.*, Vol. 208, pp. 171-175 (1993).

Ochman, H. et al., "Genetic Applications of an Inverse Polymerase Chain Reaction", *Genetics* 120:621-623 (1988).

Ohara, To et at, "'Wired' Enzyme Electrodes for Amperometric Determination of Glucose or Lactate in the Presence of Interfering Substances", *Ana/. Chem.*, vol. 66, No. 15, pp. 2451-2457 (Aug. 1994).

Ohara, T. et al., "Glucose Electrodes Based on Cross-Linked [$Os(bpY)_2CltH$ Complexed Poly(1-vinylimidazole) Films", *Ana/. Chem.*, vol. 65, pp. 3512-3517(1993).

Okabe, S. et al., "Do Photobleached Fluorescent Microtubules Move?: Re-evaluation of Fluorescence Laser Photobleaching both In Vitro and in Growing Xenopus Axon", *J. Cell Bio.*, vol. 120, No. 5, pp. 1177-1186 (1993).

Ollis, D. et al., Structure of large fragment of *E. coli* DNA polymerase I complexed with Dtmp, *Nature*, 313:762-766 (1985).

Oroskar, A. et al., "Detection of immobilized amplicons by ELISA-like techniques" *Clin. Chem.*, 42(9):1547-1555 (1996).

Patchornik, A. et al., "Photosensitive Protecting Groups" *J. Amer. Chem. Soc.*, 92(21):6333-37 (1970).

Padmaja, T., et al., "Enzymatically degradable prodrugs: a novel methodology for drug linkage." Journal of Applied Polymer Science, 85(10): p. 2108-2118(2002).

Pennisi, E., "Gene researchers hunt bargins, fixer-uppers." Science, 298(5594): p. 735-736 (2002).

Perales et al., "Enhancement of DNA, cDNA synthesis and fidelity at high temperatures by a dimeric single-stranded DNA-binding protein," Nucleic Acids Res., 31, No. 22, 6473-6480 (2003).

Perkins, T. et al., "Relaxation of a Single DNA Molecule Observed by Optical Microscopy", *Science*, 264:822-826 (May 1994).

Pethig, R. et at, "Applications of dielectrophoresis in biotechnology", *Tibtech*, vol. 15, pp. 426-432 (Oct. 1997).

Pisani, F. et at, "Domain Organization and DNA-Induced Conformational Changes of an Archaeal Family B DNA Polymerase", *Biochemistry*, vol. 35, pp. 9158-9166 (Jul. 1996).

Plakhotnik, T. et at, "Single-Molecule Spectroscopy", *Annu. Rev. Phys. Chem.*, vol. 48, pp. 181-212 (1997).

Ploem, J., Ch. 1 "Fluorescence Microscopy", Fluorescent and Luminescent Probes for Biological Activity, Mason, T. Ed., Academic Press, London, pp. 1-11 (1993).

Qin et al., "Elastomeric Light Valves," *Advanced Materials*, vol. 9, No. 5, pp. 407-410 (1997).

Qin, P. et al., "Site-Specific Labeling of RNA with Fluorophores and Other Structural Probes", *Methods*, vol. 18, No. 1, pp. 60-70 (May 1999).

Quake, S. et al., "Fluorescent Photobleaching Method for Sequencing DNA", pp. 1-10, circa 1996.

Quake, Stephen R. et al., "Methods and Apparatuses For Analyzing Polynucleotide Sequences", pending U.S. Appl. No. 09/707,737, filed Nov. 6, 2000.

Quake, S. et al., "Polymer Physics with Single Molecules of DNA" (Dept. of Physics), a colloquium by Stephen Quake, Stanford University, Feb. 22, 1996. (Presented at Laser Spectroscopy XII Intl. Conference, Italy, Jun. 1995.).

Quake, S. et al., "From Micro- to Nanofabrication with Soft Materials", *Science*, vol. 290, No. 5496, pp. 1536-1540 (Nov. 2000).

Rapp, R. et al., "LIGA micropump for gases and liquids", *Sensors and Actuators A*. vol. 40, pp. 57-61(1994).

Rasolonjatovo I. and S.R. Sarfati, "6-N-(N-methylanthranyamido)-4-oxo-hexanoic acid: a new florescent protecting group applicable to a new DNA sequencing method." Nucleosides & Nucleotides, 17(9-11): p. 2021-2025 (1998).

Rasolonjatovo, I. and Sarfati, "Development of a new DNA sequencing method: 3'-ester cleavage catalyzed by Taq DNA polymerase." Nucleosides & Nucleotides, 18(4 & 5): p. 1021-1022 (1999).

Reha-Krantz, L. et al., "Genetic and Biochemical Studies of Bacteriophage T4 DNA Polymerase 3'→5'-Exonuclease Activity", *The Journal of Biological Chemistry*, vol. 268, No. 36, pp. 27100-27108 (1993).

Reha-Krantz, L. et al., "Motif A of Bacteriophage T4 DNA Polymerase: Role in Primer Extension and DNA Replication Fidelity", *The Journal of Biological Chemistry*, vol. 269, No. 8, pp. 5635-5643 (1994).

Rigler, R, et al, "DNA-sequencing at the single molecule level." Journal of Biotechnology, 86(3): p. 161 (2001).

Rigler, R., "Fluorescence correlations, single molecule detection and large number screening—Applications in Biotechnology", *J. Biotech.*, 41: 177-186 (1995).

Ronaghi, M. et al., "A Sequencing Method Based on Real-Time Pyrophosphate", *Science*, vol. 281, pp. 363-365 (Jul. 1998).

Ronaghi, M et al., "Real-Time DNA Sequencing Using Detection of Pyrophosphate Release." *Analytical BioChemistry*, 242, No. 0432, (1996), pp. 84-89.

Rosenblum, B. et al., "New dye-labeled terminators for improved DNA sequencing patterns", *Nucleic Acids Research*, vol. 25, No. 22, pp. 4500-4504 (Nov. 1997).

Rosenblum, B. et al., "Improved single-strand DNA sizing accuracy in capillary electrophoresis", *Nucleic Acids Research*, vol. 25, No. 19, pp. 3925-3929 (Oct. 1997).

Roylance, L. et al., "A Batch-Fabricated Silicon Accelerometer", *IEEE Trans. On Elec. Dev.*, vol. ED-26, No. 12, pp. 1911-1917(1979).

Ruparel, Hameer, "Design and synthesis of a 3'-O-allyl photocleavable fluorescent nucleotide as a reversible terminator for DNA sequencing by synthesis", *PNAS*, vol. 102, No. 17, pp. 5932-5937 (Apr. 26, 2005).

Ruth, J. et al., "Nucleoside Analogues with Clinical Potential in Antivirus Chemotherapy", *Molecular Pharmacology*, 20:415-422 (1981).

Sanger, F. et al., "DNA sequencing with chain-terminating inhibitors", *PNAS*, 74(12):5463-67 (Dec. 1977).

Sarfati, S.R., et al., "Synthesis of fluorescent derivatives of 3'-O-(6-aminohexanoyl)-pyrimidine nucleosides 5'-triphosphates that act as DNA polymerase substrates reversibly tagged at C-3'." Journal of the Chemical Society, Perkin Transactions 1: Organic and Bio-Organic Chemistry, 9: p. 1163-71 (1995).

Sato, E. et al., "Bimane Conjugates of 5-Halogenouridylic Acids as Fluorogenic Substrates for Phosphodiesterase I", *J. Chem. Research (S)*, Issue 10, pp. 390-391 (1994).

Satoh, Ikuo et al., "Flow-injection determination of inorganic pyrophosphate with use of an enzyme thermistor containing immobilized inorganic pyrophosphatase", *Chemical Abstracts*, vol. 110, No. 16, pp. 409-413 (1988).

Sauer, M., et al.., "Single molecule DNA sequencing in submicrometer channels: state of the art and future prospects." Journal of Biotechnology, 86(3): p. 181-201 (2001).

Schasfoort et al., "Field-effect flow control for microfabricated fluidic networks," Science, vol. 286, pp. 942-945 (1999).

Schueller, O., et al., "Reconfigurable diffraction gratings based on elastomeric microfluidic devices", *Sensors and Actuators*, 78, pp. 149-159 (1998).

Seeger, S. et al., "Single molecule fluorescence—High Performance Molecular Diagnosis and Screening", translated from BIOforum, pp. 179-185, (Apr. 1998).

Selvin, P., "Fluorescence Resonance Energy Transfer", *Meth. In Enzymology*, vol. 246, pp. 300-335, Academic Press (1995).

Seo, Tae Seok, "Four-color DNA sequencing by synthesis on a chip using photocleavable fluorescent nucleotides", *PNAS*, vol. 102, No. 17, pp. 5926-5931 (Apr. 26, 2005).

Seo, Tae Seok, "Photocleavable fluorescent nucleotides for DNA sequencing on a chip constructed by site-specific coupling chemistry", *PNAS*, vol. 101, No. 15, pp. 5488-5493 (Apr. 13, 2004).

Shackelford, James F., "Intro. to Materials Science for Engineers," 3rd Edition, Prentice-Hall, Inc., Macmillan Publ. Co. (1992) pp. xiii-xviii Table of Contents.

Shendure et al., "Advanced sequencing technologies: Methods and goals," *Nature Reviews*, vol. 5, No. 5, pp. 335-344 (2004).

Shoji, S. et al., "Smallest Dead Volume Microvalves for Integrated Chemical Analyzing Systems", *Proceedings of Transducers '91*, IEEE, pp. 1052-1055, San Francisco (1991).

Shoji, S. et al., "Fluids for Sensor Systems." Microsystem Technology in Chemistry and Life Science, Topics in Current Chem., vol. 194, pp. 162-188, Springer-Verlag (1998).

Smith, L. et al., "Fluorescence detection in automated DNA sequence analysis", *Nature*, vol. 321, pp. 674-679 (Jun. 1986).

Smith, L. et al., "The synthesis of oligonucleotides containing an aliphatic amino group at the 5' terminus: synthesis of fluorescent DNA primers for use in DNA sequence analysis", *Nucleic Acids Res.*, vol. 13, No. 7, pp. 2399-2412 (1985).

Smith, S. et al., "Direct Mechanical Measurements of the Elasticity of Single DNA Molecules by Using Magnetic Beads", *Science* 258:1122-26(1992).

Smits, I., "Piezoelectric Micropump with Three Valves Working Peristaltically", *Sensors and Actuators*, vol. A21-A23, pp. 203-206 (1990).

Song et al., "Influence of the triplet excited state on the photobleaching kinetics of fluorescein in microscopy," Biophysics J., 70, 2959-2968 (1996).

Sproat, B. et al., "The synthesis of protected 5'-mercapto-2',5'-dideoxyribonucleoside-3' -O-phosphoramidities; uses of 5' -mercapto-oligodeosyribonucleotides", *Nucleic Acids Res.*, 15(12):4837-48 (1987).

Stocki, S. et al., "Dynamics of Bacteriophage T4 DNA Polymerase Function: Identification of Amino Acid Residues that Affect Switching between Polymerase and 3'·:'5'-Exonuclease Activities", *J. Mol. Biol.*, 254, pp. 15-28 (1995).

Strausberg, R L, et al., "The mammalian gene collection." Science, 286(5439): p. 455-7 (1999).

Sukhorukov, G.B., et al., "Assembly of polyelectrolyte multilayer films by consecutively alternating adsorption of polynucleotides and polycations", *Thin Solid Films*, 284-285, pp. 220-223 (1996).

Tasara et al., "Incorporation of reporter molecule-labeled nucleotides by DNA polymerases. II. High-density labeling of natural DNA," Nucleic Acids Res., 31, No. 10, 2636-2646 (2003).

Taveira, N. et al., "Detection of HI VI proviral DNA by PCR and hybridization with digoxigenin labeled probes", *Mol. Cell Probes*, vol. 6, No. 4, pp. 265-270 (1992).

Taylor, D. et al., "Characterization of chemisorbed monolayers by surface potential measurements", *J. Phys. D. Appl. Phys.* 24:1443-50 (1991).

Terry, S. et al., "A Gas Chromatographic Air Analyzer Fabricated on a Silicon Wafer", *IEEE Trans. on Electron Dev.*, vol. ED-26, No. 12, pp. 1880-1886 (1979).

Theisen, P. et al., "Fluorescent dye phosphoramidite labeling of oligonucleotides", *Nucleic Acids Symp. Ser.*, vol. 27, pp. 99-100 (1992).

Thompson, N. et al., "Measuring Surface Dynamics of Biomolecules by Total Internal Reflection Fluorescence with Photobleaching Recovery or Correlation Spectroscopy", *Biophys. J.*, vol. 33, pp. 435-454 (Mar. 1981).

Thompson, N. et al., "Immunoglobulin Surface-Binding Kinetics Studied by Total Internal Reflection with Fluorescence Correlation Spectroscopy", *Biophys. J.*, vol. 43, pp. 103-114 (Jul. 1983).

Thorsen, T. S.J. Maerkl, and S.R. Quake, "Microfluidic large-scale integration." Science, 298(5593): p. 580-4 (2002).

Tokunaga, M. et al., "Single Molecule Imaging of Fluorophores and Enzymatic Reactions Achieved by Objective-Type Total Internal Reflection Fluorescence Microscopy", *Biochem. And Biophys. Res. Comm.*, vol. 235, pp. 47-53 (1997).

Toneguzzo, F. et al., "Use of a Chemically Modified T7 DNA Polymerase for Manual and Automated Sequencing of Super coiled DNA", *BioTech*, vol. 6, No. 15, pp. 460-469 (1988).

Trager, R. S., "DNA sequencing—Venter's next goal: 1000 human genomes." Science, 298(5595): p. 947 (2002).

Tufte, O. et al., "Silicon Diffused-Element Piezoresistive Diaphragms", *J. Applied Phys.*, vol. 31, No. 11, pp. 3322-3327 (Nov. 1962).

Tyagi, S. et al., "Multicolor molecular beacons for allele discrimination", *Nat. Biotechnol.*, 16:49-53 (1998).

Ullman's Encyclopedia of industrial Chemistry, 6ID Edition, vol. 6, Sections 6 to 6.3, Subject: Carbon Black, Wiley-VCH (1999), pp. 350-354.

Unger et al., "Monolithic microfabricated valves and pumps by multilayer soft lithography," Science 288: 113-116 (2000).

Unger, M. et al., "Single-Molecule Fluorescence Observed with Mercury Lamp Illumination", *BioTechniques*, vol. 27, PD. 1008-1014 (Nov. 1999).

Vale, R. et al., "Direct observation of single kinesin molecules moving along microtubules", *Nature*, vol. 380, pp. 451-453, (Apr. 1996).

Van Dam, R.M. and S.R Quake, "Gene expression analysis with universal n-mer arrays." Genome Res, 12(1): p. 145-52 (2002).

Van De Pol, F. et al., "Micro-liquid handling devices: A Review", Micro System Technologies 90, 1st Intl. Conf. On Micro Electro, Opto, Mechanic Systems and Components, pp. 799-805, Berlin, Springer-Verlag, (1990).

Van Oijen et al., "Single molecule kinetics of γ exonuclease reveal base dependence and dynamic disorder," Science, 301, 1235-1238 (2003).

Venter, J.L., et al., "The sequence of the human genome." Science, 291(5507): p. 1304-1351(2001).

Vieider, C. et al., "A Pneumatically Actuated Micro Valve With a Silicone Rubber Membrane for Integration with Fluid-Handling Systems", *Proceedings of Transducers '95*, pp. 284-286, Stockholm (1995).

Walker, M.G., et al., "Prediction of gene function by genome-scale expression analysis: Prostate cancer-associated genes.": Genome Researce, 9(12): p.. 1198-1203(1999).

Wang, G. et al., "Design and Synthesis of New Fluorogenic HIV Protease Substrates Based on Resonance Energy Transfer", *Tetrahedron Lett.*, 31(45):6493-96 (1990).

Wang, M.D., et al., "Force and Velocity measured for single molecules of RNA polymerase." Science, 282(5390): p. 902-907(1998).

Washizu et al., "Molecular dielectrophoresis of biopolymers," IEEE Transactions on Industry Applications, vol. 30, No. 4, pp. 835-843 (1994).

Watkins, R. et al., "A Total Internal-Reflection Technique for the Examination of Protein Adsorption", *J. Biomed. Mater. Res.*, vol. 11, pp. 915-938 (1977).

Weber, J.L. and E.W. Myers, "Human whole-genome shotgun sequencing." Genome Research, 7(5): p. 401-409 (1997).

Webster, J. et al., "Monolithic Capillary Gel Electrophoresis Stage with On-Chip Detector", Intl. Conf. on MEMS (MEMS 96), pp. 491-496 (1996).

Wedekind, P. et al., "Scanning microphotolysis: a new photobleaching technique based on fast intensity modulation of a scanned laser beam and confocal imaging", *J. Microscopy*, vol. 176, Pt. 1, pp. 23-33 (Oct. 1994).

Weir, et al., "Hybrigel Purification: A Novel Technique for Accelerated Prepration of DNA Sequence Products for Capillary Electrophoresis and Multiplexing," Clinical Chemistry, vol. 45, No. 11, p. 2052 (1999).

Weiss, S., "Fluorescence Spectroscopy of Single Biomolecules", *Science*, vol. 283, pp. 1676-1683 (Mar. 1999).

Welch, M.B. and K. Burgess, "Synthesis of fluorescent, photolabile 3'-O-protected nucleoside triphosphates for the base addition sequencing scheme." Nucleosides & Nucleotides, 18(2): p. 197-201 (1999).

Werner et al "Progress towards single-molecule DNA sequencing: a one color demonstration." J. Biotechnol, 102(1): p. 1-14 (2003).

Williams, N. et al., "Exploring the Adenine Nucleotide Binding Sites on Mitochondrial $F_1$-ATPase with a New Photoaffinity Probe, 3'-O-(4-Benzoyl)benzoyl Adenosine 5'-Triphosphate", *J. Bioi. Chem.*, 237(6):2834-41 (1982).

Winter et al., "Direct gene expression analysis," Curr. Pharm. Biotech., 5, p. 191-197 (2004).

Wu, et al., "Synthesis and Properties of Adenosine-5'-triphosphoro-γ-1-(5-sulfonic acid)naphthyl Ethylamide: A Fluorescent Nucleotide Substrate for DNA-Dependent RNA Polymerase from *Escherichia coli*," Archives of Biochemistry and Biophysics, vol. 246, No. 2, pp. 564-571 (1986).

Wuite, G. et al., "Single-molecule studies of the effect of template tension on T7 DNA polymerase activity", *Nature*, 404:103-6 (2000).

Xia et al., "Complex optical surfaces formed by replica molding against elastomeric masters," Science vol. 273, pp. 347-349 (1996).

Xia et al. "Soft Lithography," Angew. Chem. Int. Ed. vol. 37, pp. 551-575 (1998).

Xia, G., et al., "Directed evolution of novel polymerase activities: mutation of a DNA polymerase into a efficient RNA polymerase." Proc Natl Acad Sci USA; 99(10) p. 6597-6602 (2002).

Xie, "Single molecule approach to dispersed kinetics and dynamic disorder: Probing conformational fluctuation and enzymatic dynamics," J. Chem. Physics, 117, No. 24, p. 11024-11032 (2002).

Xu, X. et al., "Direct Measurement of Single-Molecule Diffusion and Photodecomposition in Free Solution", *Science*, vol. 275, pp. 1106-1109, (Feb. 1997).

Xu, X. et al., "Long-Range Electrostatic Trapping of Single-Protein Molecules at a Liquid-Solid Interface", *Science*, vol. 281, pp. 1650-1653 (Sep. 1998).

Yang et al., "A Mems Thermopneumatic Silicone Rubber Membrane Valve", Proceedings of IEEE 10th Annual International Workshop on MicroElectro Mechanical Systems, Sensors and Actuators, vol. A64, No. 1, pp. 101-108 (1998).

Yazdi, N. et al., "Micromachined Inertial Sensors", *Proceedings of the IEEE*, vol. 86, No., pp. 1640-1659 (Aug. 1998).

Yershov, G. et al., "DNA analysis and diagnostics on oligonucleotide microchips", *Proc. Natl. Acad. Sci. USA*, vol. 93, pp. 4913-4918 (May 1996).

Young et al., "Contoured elastic-membrane microvalves for microfluidic network integration," J. Biomechanical Engineering, vol. 121, pp. 2-6 (1999).

Yu., et al., "Cyanine dye dUTP analogs for enzymatic labeling of DNA probes." Nucleic Acids Res, 22(15): p. 3226-32 (1994).

Zdeblick, M. et al., "A Microminiature Electric-To-Fluidic Valve", Transducers '87, reprinted in *Micromechanics and MEMS Classic and Seminal Papers to 1990*, IEEE Press, pp. 437-439 (1987).

Zhu, Z. et al., "Molecular Mechanism Controlling the Incorporation of Fluorescent Nucleotides into DNA by PCR ", *Cytometry*, 28:206-211(1997).

Zhu, Z. et al., "Directly labeled DNA probes using fluorescent nucleotides with different length linkers", *Nucleic Acids Res.*, vol. 22, No. 16, pp. 3418-3422 (1994).

Zuckerman, R. et al., "Efficient methods for attachment of thiol specific probes to the 3' ends of synthetic oligodeoxyribonucleotides", *Nucleic Acids Res.*, 15(13):5305-5321 (1987).

Therminator DNA Polymerase FAQ, http://www.neb.com/nebecomm/products/faqproductM0261.asp downloaded Jun. 1, 2005, 1 page.

* cited by examiner

SINGLE MOLECULE SEQUENCING OF CAPTURED NUCLEIC ACIDS

TECHNICAL FIELD OF THE INVENTION

This invention relates to methods and compositions for detecting, enumerating, and identifying nucleic acids using capture probes to capture and purify target nucleic acid in combination with single molecule sequencing of the captured or purified nucleic acid molecules.

BACKGROUND OF THE INVENTION

Knowledge of the human genome has given rise to inquiry into individual differences, as well as differences within an individual, as the basis for differences in biological function and dysfunction. Differences as small as single nucleotide polymorphisms (SNPs) or combinations of SNPs can lead to phenotypic differences, and detection of combinations of SNPs can predict the likelihood that an individual will get a specific disease or how an individual will respond to treatment.

For example, most cancers develop from a series of genomic changes, some subtle and some significant, that occur in a small subpopulation of cells. Knowledge of the sequence variations that lead to cancer will lead to an understanding of the etiology of the disease, as well as ways to treat and/or prevent it. An essential first step in understanding genomic complexity is the ability to perform high-resolution sequencing. Therefore, a true understanding of the complexities in either normal or abnormal function will require specific sequence information from large numbers of target nucleic acid molecules.

Bulk sequencing techniques are often not useful for the identification of subtle or rare nucleotide changes due to the many cloning, amplification and electrophoresis steps that complicate the process of gaining useful information regarding individual nucleotides. The ability to sequence and gain information from single molecules obtained from an individual patient is the next milestone for genomic sequencing. However, effective diagnosis and management of important diseases through single molecule sequencing is impeded by lack of cost-effective tools and methods for screening individual molecules.

There have been many proposals to develop new sequencing technologies based on single-molecule measurements, generally either by observing the interaction of particular proteins with DNA or by using ultra high resolution scanned probe microscopy. See, e.g., Rigler, et al., Biotech., 86(3):161 (2001); Goodwin, P. M., et al., Nucleosides & Nucleotides, 16(5-6):543-550 (1997); Howorka, S., et al., Nature Biotech., 19(7):636-639 (2001); Meller, A., et al., Proc. Natl. Acad., 97(3):1079-1084 (2000); Driscoll, R. J., et al., Nature, 346 (6281):294-296 (1990). A recent technique employs optical detection in a sequencing-by-synthesis reaction at the single molecule level. Braslavsky, et al., PNAS, 100: 3960-3964 (2003). The present invention provides improvements in sequencing, especially single molecule sequencing.

SUMMARY OF THE INVENTION

The invention provides methods for sequencing nucleic acids. According to the invention, sequencing is facilitated by capture of target nucleic acids to be sequenced prior to sequencing. In a preferred embodiment, target nucleic acids are sequenced at the single molecule level, resulting in sample-specific, high-throughput sequence information.

Thus, according to one aspect of the invention, sequence-specific capture probes are used to isolate target nucleic acids of interest. The target population may be composed of same-sequence nucleic acids or may be a population of mixed-sequence nucleic acids. The isolated target nucleic acids are then sequenced. In one embodiment, sequencing is performed directly on captured nucleic acids, using the capture probes as primers. Alternatively, target/probe duplex may be melted and the target nucleic acids may then be hybridized to primers for template-dependent sequencing.

In a preferred embodiment, single molecule sequencing is conducted in order to provide high-resolution, high-throughput sequence information. Template-dependent single-molecule sequencing-by-synthesis is conducted using optically-labeled nucleotides for addition to the primer or probe. Either the target (template) or the primer/probe, or both are attached to a surface that is designed to enhance optical signal detection. A particularly-preferred surface is an epoxide surface coated onto glass or fused silica. Nucleic acids are easily attached to epoxide or epoxide derivatives. A preferred method is direct amine attachment. Nucleic acids can be purchased with a 5' or 3' amine, or terminal transferase can be used to introduce a terminal amine for attachment to the epoxide ring. Alternatively, epoxide surfaces can be derivatized for nucleic acid attachment. For example, the surface can incorporate streptavidin, which binds to biotinylated nucleic acids. Either the target, primer/probe, or both can be biotinylated using known methods. Alternative surfaces include polyelectrolyte multilayers as described in Braslavasky, et al., PNAS 100: 3960-64 (2003), incorporated by reference herein. Essentially, any surface that has reduced native fluorescence and is amenable to attachment of oligonucleotides is useful for the invention.

Single molecule sequence is advantageously performed using optically-detectable labels. Especially preferred are fluorescent labels, including fluorescein, rhodamine, derivatized rhodamine dyes, such as TAMRA, phosphor, polymethadine dye, fluorescent phosphoramidite, texas red, green fluorescent protein, acridine, cyanine, cyanine 5 dye, cyanine 3 dye, 5-(2'-aminoethyl)-aminonaphthalene-1-sulfonic acid (EDANS), BODIPY, 120 ALEXA, or a derivative or modification of any of the foregoing.

The capture step prior to sequencing may be any suitable hybrid capture method. For example, capture can occur in solution, on beads (polystyrene beads), in a column (such as a chromatography column), in a gel (such as a polyacrylamide gel), or directly on the surface to be used for sequencing. An array of support-bound capture oligos can be used to hybridize specifically to a target sequence. Additionally, chromatography-based capture techniques are useful. For example, ion exchange chromatography, HPLC, gas chromatography, and gel-based chromatography all are useful. In one embodiment, gel-based capture is used in order to achieve sequence-specific capture. Using this method, multiple different sequences are captured simultaneously using immobilized probes in the gel. The target sequences are isolated by removing portions of the gel containing them and eluting target from the gel portions for sequencing.

In an alternative embodiment, the target nucleic acid molecule either includes, or is modified to include, an adaptor sequence (such as a polyadenylation region) that is complementary to a portion of a capture probe in order to aid in the capture of the target. A preferred embodiment comprises an immobilized capture probe having a sequence that hybridizes (e.g., is complementary to) with the adaptor sequence. Methods of the invention are conducted by contacting capture probes with a sample comprising target nucleic acid molecules under conditions suitable for specific hybridization between the target nucleic acid molecule and immobilized capture probe, thereby forming target/capture probe duplex. A wash step removes debris and unhybridized nucleic acid in the sample. In one embodiment, target nucleic acid is sequenced using the capture probe as a primer for template-dependent sequencing-by-synthesis. In another embodiment, the target/capture probe duplex is melted to release target nucleic acid. The resulting purified target population is sequenced as described below.

If target nucleic acid is melted off the capture probe, the targets are either attached to a surface for sequencing or hybridized to a primer that has been attached to the surface. Surface attachment of oligonucleotides for sequencing can be direct or indirect. For example, nucleic acids are attached to an epoxide surface via a direct amine linkage as described below. Alternatively, the surface is prepared with a binding partner, the opposite of which is attached to the nucleic acid. For example, the surface can be streptavidinated and biotinylated nucleic acids can be used to form an attachment at the surface. Other binding pairs (e.g., antibody/antigen, such as digoxigenen/anti-digoxigenen and dinitorphenol/anti-dinitrophenol) can also be used.

In a preferred embodiment, the invention contemplates optical sequencing. Preferably, template-dependent sequencing-by-synthesis is conducted using optically-detectable labels. Optimal labels include fluorescent labels as described in detail below. The surface is prepared to minimize background for optical detection of incorporated nucleotides. Primer/template duplex attached to the surface is exposed to labeled nucleoside triphosphates in the presence of a suitable nucleotide polymerizing enzyme, under conditions suitable for the enzyme to add at least one nucleotide to the primer in template-dependent manner, and the added nucleotide is detected, thereby identifying at least one nucleotide in at least one attached target nucleic acid molecule.

As will be appreciated by one skilled in the art, individual features of the invention may be used separately or in any combination. A detailed description of embodiments of the invention is provided below. Other embodiments of the invention are apparent upon review of the detailed description that follows.

DETAILED DESCRIPTION OF THE INVENTION

The present invention provides methods for sequencing nucleic acids. In a preferred embodiment, the invention comprises the use of single molecule sequencing of hybrid-captured nucleic acids. Methods of the invention are highly parallel and are amenable to multiplexing. As a result, biological samples can be rapidly analyzed over a broad dynamic range.

Methods of the invention comprise hybrid-capturing target nucleic acid and sequencing the captured targets. Captured target nucleic acids can be sequenced directly using the capture probe as a primer for template-dependent synthesis. Thus, capture probes are bound to a surface and exposed to sample nucleic acids. Complementary binding of target nucleic acid and probes occurs and the remaining nucleic acid and other sample contents are washed from the surface. Sequencing then takes place essentially as described below. In one alternative, target nucleic acids are isolated by contacting a sample containing target nucleic acid molecules with immobilized capture probes capable of hybridizing to target nucleic acid. The surface is washed to remove non-target nucleic acids and other debris, and the targets are then melted off the target/capture probe duplex. After an optional wash, the targets are bound to a surface for sequencing essentially as described below. Target nucleic acid molecules preferably are analyzed using single molecule sequencing techniques described below. In a preferred embodiment, target nucleic acid is modified by addition of a polynucleotide sequence that specifically hybridizes to a complementary portion of a primer for nucleic acid synthesis. For example, targets can be polyadenylated and captured using poly-dT probes/primers for sequencing.

Target Nucleic Acid Molecules

Target nucleic acids include deoxyribonucleic acid (DNA) and/or ribonucleic acid (RNA). Target nucleic acids can be isolated or can be captured in situ. In a preferred alternative, target nucleic acid is isolated from a biological sample containing a variety of other components, such as proteins, lipids and non-target nucleic acids. Target nucleic acid molecules can be obtained from any cellular material, obtained from an animal, plant, bacterium, virus, fungus, or any other cellular organism. Target nucleic acids may be obtained directly from an organism or from a biological sample obtained from an organism, e.g., from blood, urine, cerebrospinal fluid, seminal fluid, saliva, sputum, stool and tissue. Any tissue or body fluid specimen may be used as a source for nucleic acid for use in the invention. Nucleic acid molecules may also be isolated from cultured cells, such as a primary cell culture or a cell line. The cells from which target nucleic acids are obtained can be infected with a virus or other intracellular pathogen.

A sample can also be total RNA extracted from a biological specimen, a cDNA library, or genomic DNA. Nucleic acid typically is fragmented to produce suitable fragments for capture and/or purification and analysis. In one embodiment, nucleic acid from a biological sample is fragmented by sonication. Test samples can be obtained as described in U.S. Patent Application 2002/0190663 A1, published Oct. 9, 2003, the teachings of which are incorporated herein in their entirety. Generally, nucleic acid can be extracted from a biological sample by a variety of techniques such as those described by Maniatis, et al., Molecular Cloning: A Laboratory Manual, Cold Spring Harbor, N.Y., pp. 280-281 (1982). Generally, target nucleic acid molecules can be from about 5 bases to about 20 kb. Nucleic acid molecules may be single-stranded, double-stranded, or double-stranded with single-stranded regions (for example, stem- and loop-structures).

A biological sample as described herein may be homogenized or fractionated in the presence of a detergent or surfactant. The concentration of the detergent in the buffer may be about 0.05% to about 10.0%. The concentration of the detergent can be up to an amount where the detergent remains soluble in the solution. In a preferred embodiment, the concentration of the detergent is between 0.1% to about 2%. The detergent, particularly a mild one that is nondenaturing, can act to solubilize the sample. Detergents may be ionic or nonionic. Examples of nonionic detergents include triton, such as the Triton® X series (Triton® X-100 t-Oct-$C_6H_4$—($OCH_2$—$CH_2$)$_x$OH, x=9-10, Triton® X-100R, Triton® X-114 x=7-8), octyl glucoside, polyoxyethylene(9)dodecyl ether, digitonin, IGEPAL® CA630 octylphenyl polyethylene glycol, n-octyl-beta-D-glucopyranoside (betaOG), n-dodecyl-beta, Tween® 20 polyethylene glycol sorbitan monolaurate, Tween® 80 polyethylene glycol sorbitan monooleate, polidocanol, n-dodecyl beta-D-maltoside (DDM), NP-40 nonylphenol polyethylene glycol, C12E8 (octaethylene glycol n-dodecyl monoether), hexaethyleneglycol mono-n-tetradecyl ether (C14EO6), octyl-beta-thioglucopyranoside (octyl thioglucoside, OTG), Emulgen, and polyoxyethylene 10 lauryl ether (C12E10). Examples of ionic detergents (anionic or cationic)

include deoxycholate, sodium dodecyl sulfate (SDS), N-lauroylsarcosine, and cetyltrimethylammoniumbromide (CTAB). A zwitterionic reagent may also be used in the purification schemes of the present invention, such as Chaps, zwitterion 3-14, and 3-[(3-cholamidopropyl)dimethylammonio]-1-propanesulfonate. It is contemplated also that urea may be added with or without another detergent or surfactant.

Lysis or homogenization solutions may further contain other agents, such as reducing agents. Examples of such reducing agents include dithiothreitol (DTT), β-mercaptoethanol, DTE, GSH, cysteine, cysteamine, tricarboxyethyl phosphine (TCEP), or salts of sulfurous acid.

Preferred buffer concentration is from about 5 mM to about 500 mM in solution or in solution with the sample. The buffer concentration in the lysing solution can be between about 10 mM and 300 mM.

Subsequent to exposure to a homogenization solution, samples may be further homogenized by mechanical means. Mechanical blenders, rotor-stator homogenizers, or shear-type homogenizers may be employed. Alternatively, the tissue can be homogenized in the lysis solution, and the tissue remains separated by settling, centrifugation, or filtration. These remains could then be treated with homogenization solution and extraction conditions as described above.

Target nucleic acid molecules can include or be modified to include an adaptor sequence that is complementary to the immobilized capture probe. The adaptor sequence and immobilized capture probe are chosen such that the target nucleic acid molecule comprising the adaptor sequence can hybridize to the immobilized capture probe. Typically, the adaptor sequence is a homopolymer, such as oligo(dA), and the corresponding immobilized capture probe includes an oligo(dT) sequence. The adaptor sequence may be endogenously contained within the target nucleic acid molecule, for example, the adaptor sequence can be a sequence of interest in the target nucleic acid molecule. Alternatively, the adaptor sequence can comprise vector sequence.

In one embodiment, a universal probe is used as the immobilized capture probe and the target nucleic acid molecules are modified with an adaptor comprising a sequence complementary to the universal probe, thereby allowing the modified nucleic acid molecules to hybridize to the immobilized probe.

The adaptor sequence and complementary sequence within the immobilized capture probe are of a length suitable for hybridizing the target nucleic acid molecule to the immobilized capture probe to thereby capture target nucleic acid molecules to form target probe/duplexes. The target probe/duplexes are also sufficiently stable to permit optional washing of the duplexes to remove any remaining components of the biological sample, including non-target nucleic acids. The sequence of the adaptor and the complementary sequence of the immobilized capture probe can be about 10 to about 100, and preferably 50, nucleotides in length. The adaptor sequence and complementary immobilized capture sequence can be of the same length or of different lengths. It is routine in the art to adjust probe length and/or oligonucleotide length to optimize hybridization.

The adaptor sequence can be attached to the nucleic acid molecules with an enzyme. The enzyme can be a ligase or a polymerase. The ligase can be an enzyme capable of ligating an oligonucleotide (RNA or DNA) to the nucleic acid molecules. Suitable ligases include, for example, T4 DNA ligase and T4 RNA ligase (such ligases are available commercially, from New England BioLabs (on the World Wide Web at NEB.com). In a preferred embodiment, the target nucleic acid molecules are dephoyshorylated before ligating the adaptors. Methods for using ligases are well known in the art.

The polymerase can be any enzyme capable of adding nucleotides to the target nucleic acid molecules. The polymerase can be, for example, poly(A) polymerase, including yeast poly(A) polymerase, commercially available from USB (on the World Wide Web at USBweb.com), terminal deoxyribonucleotidyl transferase (TdT), and the like. The polymerases can be used according to the manufacturer's instructions.

Purifying Target Nucleic Acid Molecules

As described herein, target nucleic acid molecules can be purified by contacting a sample containing the target molecules with one or more classes of immobilized capture probes. Where more than one target molecule is to be purified, the different target molecules can have the same or different adaptor sequences. A given class of immobilized capture probe is selected to hybridize to target nucleic acid molecules containing the corresponding adaptor sequence, under conditions suitable for the target nucleic acid molecule to hybridize to the immobilized capture probe, thereby forming target/probe duplexes. A variety of capture probes can be used to purify the target nucleic acid molecules. The capture probes typically comprise a nucleic acid with a nucleotide sequence with substantial complementarity to a region of the target nucleic acid molecule, so that the target nucleic acid molecule can hybridize to the capture probe. Complementarity between target nucleic acid molecules and the capture probes need only be sufficient to specifically bind the target nucleic acid molecule, and thus, to effectuate purification of the target nucleic acid molecule from a test sample. Probes suitable for use in the present invention include those formed from nucleic acids, such as RNA and/or DNA, nucleic acid analogues, modified nucleic acids, and chimeric probes of a mixed class comprising a nucleic acid with another organic component such as peptide nucleic acids. Capture probes can be single stranded or double stranded. Preferably, the length of the capture probe is at least 5 nucleotides, more preferably between about 5 and about 100 nucleotides, but the length can be up to several thousand nucleotides. Additional probes are described in U.S. Patent application 2002/0119480 A1, published Aug. 29, 2002, the teachings of which are incorporated herein in their entirety.

Capture probes can be coupled to agarose, dextrans, cellulose, beads, microparticles, and starch polymers using cyanogen bromide or cyanuric chloride activation. Particularly useful beads and microparticles are described in U.S. Patent Application 2003/0190663 A1, published Oct. 9, 2003, the teachings of which are incorporated herein in their entirety. Polymers containing carboxyl groups can be coupled to synthetic capture probes having primary amine groups using carbodiimide coupling. Polymers containing primary amines can be coupled to amine-containing probes with glutaraldehyde or cyanuric chloride. Polymers can also be modified with thiol-reactive groups that can be coupled to thiol-containing probes. Many other suitable methods can be found in the literature (Wong, Chemistry of Protein Conjugation and Cross-Linking, CRC Press, Boca Raton, Fla. 1993). Methods for covalently attaching the capture probes to polymerizable chemical groups are also described in U.S. 2002/0119480 A1, the teachings of which are incorporated herein. In addition, as described in U.S. 2002/0119480 A1, nucleic acids can be attached to particles which themselves can be incorporated into electrophoretic media.

To purify target nucleic acid molecules, the test sample can be contacted, for example, with an electrophoretic medium that comprises at least one immobilized capture probe. An electric field is applied across the electrophoretic medium so that negatively charged molecules can migrate through the medium. The non-target components of the test sample pass into the electrophoresis buffer, while the target nucleic acid molecules are captured by hybridizing to the capture probes within the electrophoretic medium (forming target/probe duplexes). The buffer used for the electrophoresis step (containing the non-target components of the test sample) can be replaced with fresh buffer and current applied across the electrophoretic medium to denature the complex, thereby releasing the target nucleic acid molecule from the capture probe. The released target nucleic acid molecule can be eluted by applying a reversed electric field.

The method of the present invention is suitable for multiplexing. As described above, a sample can include more than one target nucleic acid molecule. If adapters are used, the different target nucleic acid molecules can have the same or different adaptor sequences. In a multiplexing reaction, where the target nucleic acid molecules contain different adaptor sequences, the test sample is contacted with two or more classes of immobilized capture probes as described above. Target nucleic acid molecules are captured by their respective immobilized capture probes. The captured target nucleic acid molecules can be released as described above. Other methods for capturing and purifying target nucleic acid molecules are described in U.S. 2002/0119480 A1, the teachings of which are incorporated herein.

Attaching Target Nucleic Acid Molecules to a Surface

In a preferred embodiment, target nucleic acid molecules are attached to a surface and subjected to analysis by single molecules sequencing. Target nucleic acid molecules are attached to the surface such that they are individually optically resolvable. Substrates for use in the invention can be two- or three-dimensional and can comprise a planar surface (e.g., a glass slide) or can be shaped. A substrate can include glass (e.g., controlled pore glass (CPG)), quartz, plastic (such as polystyrene (low cross-linked and high cross-linked polystyrene), polycarbonate, polypropylene and poly(methymethacrylate)), acrylic copolymer, polyamide, silicon, metal (e.g., alkanethiolate-derivatized gold), cellulose, nylon, latex, dextran, gel matrix (e.g., silica gel), polyacrolein, or composites.

Suitable three-dimensional substrates include, for example, spheres, microparticles, beads, membranes, slides, plates, micromachined chips, tubes (e.g., capillary tubes), microwells, microfluidic devices, filters, or any other structure suitable for anchoring a nucleic acid. Substrates can include planar arrays or matrices capable of having regions that include populations of target nucleic acids or primers. Examples include nucleoside-derivatized CPG and polystyrene slides; derivatized magnetic slides; polystyrene grafted with polyethylene glycol, and the like.

In one embodiment, a substrate is coated to allow optimum optical processing and nucleic acid attachment. Surfaces for use in the invention are treated to reduce background. Exemplary coatings include epoxides, and derivatized epoxides (e.g., with a binding molecule, such as streptavidin). The surface can also be treated to improve the positioning of attached nucleic acids (e.g., target nucleic acid molecules, primers, or target molecule/primer complexes) for analysis. As such, a surface according to the invention can be treated with one or more charge layers (e.g., a negative charge) to repel a charged molecule (e.g., a negatively charged labeled nucleotide). For example, a substrate according to the invention can be treated with polyallylamine followed by polyacrylic acid to form a polyelectrolyte multilayer. The carboxyl groups of the polyacrylic acid layer are negatively charged and thus repel negatively charged labeled nucleotides, improving the positioning of the label for detection. Coatings or films applied to the substrate should be able to withstand subsequent treatment steps (e.g., photoexposure, boiling, baking, soaking in warm detergent-containing liquids, and the like) without substantial degradation or disassociation from the substrate.

Examples of substrate coatings include, vapor phase coatings of 3-aminopropyltrimethoxysilane, as applied to glass slide products, for example, from Molecular Dynamics, Sunnyvale, Calif. In addition, generally, hydrophobic substrate coatings and films aid in the uniform distribution of hydrophilic molecules on the substrate surfaces. Importantly, in those embodiments of the invention that employ substrate coatings or films, the coatings or films that are substantially non-interfering with primer extension and detection steps are preferred. Additionally, it is preferable that any coatings or films applied to the substrates either increase target molecule binding to the substrate or, at least, do not substantially impair target binding.

Various methods can be used to anchor or immobilize the target nucleic acid molecule to the surface of the substrate. The immobilization can be achieved through direct or indirect bonding to the surface. The bonding can be by covalent linkage. See, Joos et al., Analytical Biochemistry 247:96-101, 1997; Oroskar et al., Clin. Chem. 42:1547-1555, 1996; and Khandjian, Mole. Bio. Rep. 11:107-115, 1986. A preferred attachment is direct amine bonding of a terminal nucleotide to an epoxide integrated on the surface. The bonding also can be through non-covalent linkage. For example, biotin-streptavidin (Taylor et al., J. Phys. D. Appl. Phys. 24:1443, 1991) and digoxigenin with anti-digoxigenin (Smith et al., Science 253: 1122, 1992) are common tools for anchoring nucleic acids to surfaces and parallels. Alternatively, the attachment can be achieved by anchoring a hydrophobic chain into a lipid monolayer or bilayer. Other methods for known in the art for attaching nucleic acid molecules to supports also can be used.

In a preferred embodiment, surfaces for oligonucleotide attachment are coated with an epoxide. An epoxide may be deposited by many methods known in the art. An epoxy silane surface is preferred. Different molecules or combinations of molecules may serve to link the epoxide to a surface. Ideally, a surface will be coated with an even distribution of epoxides prior to introduction of target nucleic acid molecules. Target nucleic acid molecules can be directly or indirectly linked to an epoxide. In a direct attachment embodiment, the epoxide is introduced to a nucleic acid bearing an amine group. In a preferred embodiment, terminal transferase is used to add an amine-terminated nucleotide to a nucleic acid to be attached to the surface.

When biotin-streptavidin linkage is used to anchor the nucleic acids, the nucleic acids can be biotinylated, while one surface of the substrates can be coated with streptavidin. Surface density of the nucleic acid molecules can be controlled by adjusting the concentration of the streptavidin applied to the surface. Reagents for biotinylating a surface can be obtained, for example, from Vector Laboratories. Alternatively, biotinylation can be performed with BLCPA: EZ-Link Biotin LC-PEO-Amine (Pierce, Cat. 21347), or any other known or convenient method. In some embodiments, labeled streptavidin of very low concentration (e.g., in the µM, nM or pM range) is used to coat the substrate surface prior to anchoring. This can facilitate immobilization of the nucleic acid with single molecule resolution.

Other examples of linkers include antigen/antibody, digoxigenin/anti-digoxigenin, dinitrophenol, fluorescein, and other haptens known in the art. Alternatively, the nucleic acid may contain other binding moieties that result in a conformational change of the epoxide ring and result in a direct attachment of the target nucleic acid molecules to the opened epoxide ring.

Alternatively, primers may be immobilized on the surface. A terminus of one or more primers may be modified to carry a linker moiety for tethering the primers to the surface or may be directly attached to the surface. Target nucleic acid molecules containing primer complementary sequence are then hybridized to the attached primer. Methods for attaching nucleic acid such as primer to the surface of a substrate are described in detail above.

In order to inhibit non-specific binding of molecules to a surface, the surface can be treated with a passivating (blocking) agent. Preferred blocking strategies include exposing the surface to a non-detectable molecule that adheres to the surface or changes the chemical properties of the surface such that non-specific binding is reduced. In methods in which optically-detectable labels are used, one way to block or passivate the surface is to expose the surface to unlabeled molecules of the same type as those that are labeled. The unlabeled molecules will out-compete labeled molecules for non-specific binding on the surface, thus reducing background due to non-specific label. Other strategies involve treating the surface with phosphate, Tris, a sulfate, or an amine that interacts with the surface to prevent non-specific binding. Non-reactive proteins are also appropriate. In a preferred embodiment, a matrix of blocking reagents is provided on the surface in order to provide a highly washable, low non-specific background surface. In some embodiments, blocking reagents are chosen to provide electrostatic repulsion of highly anionic nucleoside triphosphates.

Blocking agents may be introduced or reintroduced at any time during the analysis. Also, in some embodiments, blocking agents may be used to pre-treat the surface prior to exposing the substrate to target nucleic acid molecules or primers. In addition, blocking agents, such as a detergent (e.g., Tris) may be included in some or all wash steps in order to passivate the surface during incubation periods and/or washes.

Surface charge can be manipulated to achieve ideal conditions during both nucleic acid attachment and primer extension. For example, during the loading phase where the nucleic acid (target nucleic acid molecule or primer) is bound to the surface, the salt concentration of the solution may be increased in order to create a more positive surface charge on the substrate to facilitate reaction between the amine portion of the nucleic acid and the epoxide ring. Conversely, after the nucleic acid has been secured to the surface, the salt concentration of the solution can lowered in order to repel the nucleic acid from the surface of the substrate thereby sterically conforming the nucleic acid for annealing and sequence analysis.

In another embodiment, the substrate includes a layer of polyanions and nucleic acid molecules anchored on the layer of polyanions. Accordingly, nucleic acids are positioned to avoid being substantially parallel (e.g., is hindered from lying down on the layer of polyanions.) In some embodiments, the surface of a substrate is pretreated to create a surface chemistry that facilitates nucleic acid attachment and subsequent annealing and sequence analysis. In some of these embodiments, the substrate surface is coated with a polyelectrolyte multilayer (PEM). In some cases, biotin can be applied to the PEM, followed by application of streptavidin. The substrate can then be used to attach biotinylated target nucleic acid molecules.

In some embodiments, multiple layers of alternating positive and negative charges are used. In the case of incompletely-charged surfaces, multiple-layer deposition tends to increase surface charge to a well-defined and stable level. For example, surfaces can be coated with a PEM for attachment of primers via light-directed spatial attachment. Alternatively, target nucleic acid molecules can be attached to a PEM-coated surface chemically. PEM formation has been described in Decher et al. (Thin Solid Films, 210:831-835, 1992), the teachings of which are incorporated herein. PEM formation proceeds by the sequential addition of polycations and polyanions, which are polymers with many positive or negative charges, respectively. Upon addition of a polycation to a negatively-charged surface, the polycation deposits on the surface, forming a thin polymer layer and reversing the surface charge. Similarly, a polyanion deposited on a positively charged surface forms a thin layer of polymer and leaves a negatively charged surface. Alternating exposure to poly(+) and poly(−) generates a polyelectrolyte multilayer structure with a surface charge determined by the last polyelectrolyte added. This can produce a strongly-negatively-charged surface, repelling the negatively-charged nucleotides. Detailed procedures for coating a substrate with PEM for immobilizing nucleic acid are described in U.S. patent application Ser. No. 11/137,928, field May 25, 2005.

In another aspect of the invention, the substrate may be prepared by, for example, coating with a chemical that increases or decreases hydrophobicity or coating with a chemical that allows covalent linkage of the primers. Some chemical coatings may both alter the hydrophobicity and allow covalent linkage. Hydrophobicity on a solid substrate may readily be increased by silane treatment or other treatments known in the art. Linker molecules adhere to the surface and comprise a functional moiety that reacts with biomolecules. Many such linkers are readily available and known in the art. For example, substrates or supports are modified with photolabile-protected hydroxyl groups, alkoxy or aliphatic derivatized hydroxyl groups, or other chemicals. A preferred coating that both decreases hydrophobicity and provides linkers is poly(ethyleneimine).

Methods of the invention also optionally include a surface drying step. In some embodiments, the surface is exposed to a drying agent prior to, during and/or after a chemical reaction, such as a nucleotide incorporation step. Examples of preferred drying agents include, without limitation, phosphate buffer, an alcohol (such as, for example, EtOH), air and/or $N_2$.

Analyzing Attached Target Nucleic Acid Molecules

As described herein, attached target nucleic acid molecules are analyzed by single molecule sequencing. At least one nucleotide is identified in at least one attached target nucleic acid molecule. Target molecules are hybridized to a primer to form nucleic acid target molecule/primer duplex on a surface. As described above, either the target nucleic acid molecule or the primer, or both, is/are attached to the surface. Thereafter, template-dependent primer extension is conducted to identify at least one nucleotide of the hybridized nucleic acid molecule using a nucleotide polymerizing enzyme and a nucleotide (e.g., dATP, dTTP, dUTP, dCTP and/or a dGTP) or a nucleotide analog. Incorporation of a nucleotide or a nucleotide analog is detected at discrete locations on the surface. Nucleic acid target molecule/primer duplexes, as well as the incorporated nucleotides, are individually resolvable in single molecule embodiments. Alternatively, bulk signal from mixed nucleic acid populations or clonal populations of nucleic acids, are obtained.

Fast reagent application and removal is another advantage of the invention. For example, concentrations of nucleotides and/or other reaction reagents can be alternated at different time points. This is a particularly useful feature in an embodiment comprising introducing one or more single species of nucleotide individually. This could lead to increased incorporation rates and sensitivity. For example, when all four types of nucleotides are simultaneously present in the reaction to monitor dynamic incorporation of nucleotides, concentrations of the each of the respective nucleotides can be alternated between a first and a second range. This leads to both better visualization of the signal when low concentrations of nucleotides are present, and increased polymerization rate when higher concentrations of nucleotides are present.

The target nucleic acid can comprise or can be modified to comprise a sequence that is sufficiently complementary to a primer to hybridize to the primer to allow template dependent addition of nucleotides to the hybridized primer. The sequence complementary to the primer can be the same as the previously described adaptor sequence. Therefore, the immobilized capture probe and the primer can comprise the same sequence. The primer sequence can be about 10 to about 1000 nucleotides in length. The primer sequence and complementary target nucleic acid molecule sequence can be of the same length or of different lengths. Conditions for hybridizing primers to nucleic acid targets are well known. The annealing reaction is performed under conditions which are stringent enough to guarantee sequence specificity, yet sufficiently permissive to allow formation of stable hybrids at an acceptable rate. The temperature and length of time required for primer annealing depend upon several factors including the base composition, length and concentration of the primer, and the nature of the solvent used, e.g., the concentration of cosolvents such as DMSO (dimethylsulfoxide), formamide, or glycerol, and counterions such as magnesium. Typically, hybridization (annealing) between primers and target nucleic acids is carried out at a temperature that is approximately 5 to 10° C. below the melting temperature of the target-primer hybrid in the annealing solvent. Typically, the annealing temperature is in the range of 55 to 75° C. and the primer concentration is approximately 0.2 μM. Under such conditions, the annealing reaction is usually complete within a few seconds.

Methods according to the invention include conducting a primer extension reaction, such as exposing the nucleic acid/primer complexes to polymerase and one or more nucleotides under conditions sufficient to extend the primer by at least one base. Sequencing, as used herein can be performed such that one or more nucleotides are identified in one or more nucleic molecules. Methods according to the invention also include the step of compiling a sequence of the molecule (nucleic acid) based upon sequential incorporation of the extension bases into the primer.

In the analyzing step, the hybridized nucleic acid molecules can be sequenced using single molecule sequencing as described, for example, in U.S. patent application Ser. No. 11/137,928, filed May 25, 2005 and/or and described in U.S. Pat. No. 6,780,591, the teachings of which are incorporated herein in their entirety. Polymerases useful in the invention include any nucleic acid polymerase capable of catalyzing a template-dependent addition of a nucleotide or nucleotide analog to a primer. Depending on the characteristics of the target nucleic acid, a DNA polymerase, an RNA polymerase, a reverse transcriptase, or a mutant or altered form of any of the foregoing can be used. According to one aspect of the invention, a thermophilic polymerase is used, such as ThermoSequenase®, 9°N™, Therminator™, Taq, Tne, Tma, Pfu, Tfl, Tth, Tli, Stoffel fragment, Vent™ and Deep Vent™ DNA polymerase.

The target nucleic acid molecule/primer complexes are contacted with dNTPs in the presence of the polymerase under conditions such that the polymerase catalyzes template-dependent addition of a dNTP to the 3' terminus of the primer. The dNTP can be detectably labeled, as described herein, and the nucleotide is identified by detecting the presence of the incorporated labeled nucleotide. As described above, unincorporated labeled dNTPs can be removed from the surface prior to detecting the incorporated labeled dNTP. The process can be repeated one or more times, wherein the template/primer complex(es) are provided with additional dNTPs, in the presence of a polymerase, followed by removing the unincorporated labeled dNTPs and detecting the incorporated labeled dNTP. The sequence of the template is determined by compiling the detected (identified) dNTPs. In this manner, the entire sequence of one or more templates can be determined. In addition, by using single molecule sequencing techniques, determining the sequence for each nucleic acid molecule attached to the surface provides the number of different or unique nucleic acid molecules in the sample. Furthermore, the number of copies of each nucleic acid sequences in a biological sample is also provided.

In order to allow for further extension and detection of subsequently added fluorophore-labeled nucleotides, the fluorophore of the incorporated nucleotide can be removed from the nucleotide incorporated into the primer. For example, the optical label (e.g., fluorescent label) can be destroyed by photochemical destruction as described in U.S. Pat. No. 6,780,591, the teachings of which are incorporated herein in their entirety. This cycle can be repeated a large number of times if sample losses are avoided. In one embodiment, such losses will be avoided by attaching the target nucleic acid molecules or primers to a surface of an array device, for example a microscope slide, and transferring the entire array device between a reaction vessel and the fluorescent reader.

The extension reactions are carried out in buffer solutions which contain the appropriate concentrations of salts, dNTP (s) and nucleotide polymerizing enzyme required for the enzyme mediated extension to proceed. For additional guidance regarding such conditions see, for example, Sambrook et al., (1989, Molecular Cloning, A Laboratory Manual, Cold Spring Harbor Press, NY); and Ausubel et al. (1989, Current Protocols in Molecular Biology, Green Publishing Associates and Wiley Interscience, NY).

Nucleotides particularly useful in the invention comprise detectable labels. Labeled nucleotides include any nucleotide that has been modified to include a label that is directly or indirectly detectable. Preferred labels include optically-detectable labels, including fluorescent labels or fluorophores, such as fluorescein, rhodamine, cyanine, cyanine-5 dye, cyanine-3 dye, or a derivative or modification of any of the foregoing, and also include such labeling systems as hapten labeling. Accordingly, methods of the invention further provide for exposing the primer/target nucleic acid complex to a digoxigenin, a fluorescein, an alkaline phosphatase or a peroxidase.

The sequencing can be optimized to achieve rapid and complete addition of the correct nucleotide to primers in primer/template complexes, while limiting the misincorporation of incorrect nucleotides. For example, dNTP concentrations may be lowered to reduce misincorporation of incorrect nucleotides into the primer. $K_m$ values for incorrect dNTPs can be as much as 1000-fold higher than for correct nucleotides, indicating that a reduction in dNTP concentrations can reduce the rate of misincorporation of nucleotides. Thus, in a preferred embodiment of the invention the concentration of dNTPs in the sequencing reactions are approximately 5-20 µM.

In addition, relatively short reaction times can be used to reduce the probability of misincorporation. For an incorporation rate approaching the maximum rate of about 400 nucleotides per second, a reaction time of approximately 25 milliseconds will be sufficient to ensure extension of 99.99% of primer strands.

Detection

Any detection method may be used that is suitable for the type of label employed. Thus, exemplary detection methods include radioactive detection, optical absorbance detection, e.g., UV-visible absorbance detection, optical emission detection, e.g., fluorescence or chemiluminescence. For example, extended primers can be detected on a substrate by scanning all or portions of each substrate simultaneously or serially, depending on the scanning method used. For fluorescence labeling, selected regions on a substrate may be serially scanned one-by-one or row-by-row using a fluorescence microscope apparatus, such as described in Fodor (U.S. Pat. No. 5,445,934) and Mathies et al. (U.S. Pat. No. 5,091,652). Devices capable of sensing fluorescence from a single molecule include scanning tunneling microscope (siM) and the atomic force microscope (AFM). Hybridization patterns may also be scanned using a CCD camera (e.g., Model TE/CCD512SF, Princeton Instruments, Trenton, N.J.) with suitable optics (Ploem, in Fluorescent and Luminescent Probes for Biological Activity Mason, T. G. Ed., Academic Press, Landon, pp. 1-11 (1993), such as described in Yershov et al., Proc. Natl. Aca. Sci. 93:4913 (1996), or may be imaged by TV monitoring. For radioactive signals, a phosphorimager device can be used (Johnston et al., Electrophoresis, 13:566, 1990; Drmanac et al., Electrophoresis, 13:566, 1992; 1993). Other commercial suppliers of imaging instruments include General Scanning Inc., (Watertown, Mass. on the World Wide Web at genscan.com), Genix Technologies (Waterloo, Ontario, Canada; on the World Wide Web at confocal.com), and Applied Precision Inc. Such detection methods are particularly useful to achieve simultaneous scanning of multiple attached target nucleic acids.

The present invention provides for detection of molecules from a single nucleotide to a single target nucleic acid molecule. A number of methods are available for this purpose. Methods for visualizing single molecules within nucleic acids labeled with an intercalating dye include, for example, fluorescence microscopy. For example, the fluorescent spectrum and lifetime of a single molecule excited-state can be measured. Standard detectors such as a photomultiplier tube or avalanche photodiode can be used. Full field imaging with a two-stage image intensified COD camera also can be used. Additionally, low noise cooled CCD can also be used to detect single fluorescent molecules.

The detection system for the signal may depend upon the labeling moiety used, which can be defined by the chemistry available. For optical signals, a combination of an optical fiber or charged couple device (CCD) can be used in the detection step. In those circumstances where the substrate is itself transparent to the radiation used, it is possible to have an incident light beam pass through the substrate with the detector located opposite the substrate from the target nucleic acid. For electromagnetic labeling moieties, various forms of spectroscopy systems can be used. Various physical orientations for the detection system are available and discussion of important design parameters is provided in the art.

A number of approaches can be used to detect incorporation of fluorescently-labeled nucleotides into a single nucleic acid molecule. Optical setups include near-field scanning microscopy, far-field confocal microscopy, wide-field epi-illumination, light scattering, dark field microscopy, photoconversion, single and/or multiphoton excitation, spectral wavelength discrimination, fluorophore identification, evanescent wave illumination, and total internal reflection fluorescence (TIRF) microscopy. In general, certain methods involve detection of laser-activated fluorescence using a microscope equipped with a camera. Suitable photon detection systems include, but are not limited to, photodiodes and intensified CCD cameras. For example, an intensified charge couple device (ICCD) camera can be used. The use of an ICCD camera to image individual fluorescent dye molecules in a fluid near a surface provides numerous advantages. For example, with an ICCD optical setup, it is possible to acquire a sequence of images (movies) of fluorophores.

Some embodiments of the present invention use TIRF microscopy for two-dimensional imaging. TIRF microscopy uses totally internally reflected excitation light and is well known in the art. See, e.g., the World Wide Web at nikon-instruments.jp/eng/page/products/tirf.aspx. In certain embodiments, detection is carried out using evanescent wave illumination and total internal reflection fluorescence microscopy. An evanescent light field can be set up at the surface, for example, to image fluorescently-labeled nucleic acid molecules. When a laser beam is totally reflected at the interface between a liquid and a solid substrate (e.g., a glass), the excitation light beam penetrates only a short distance into the liquid. The optical field does not end abruptly at the reflective interface, but its intensity falls off exponentially with distance. This surface electromagnetic field, called the "evanescent wave", can selectively excite fluorescent molecules in the liquid near the interface. The thin evanescent optical field at the interface provides low background and facilitates the detection of single molecules with high signal-to-noise ratio at visible wavelengths.

The evanescent field also can image fluorescently-labeled nucleotides upon their incorporation into the attached target nucleic acid target molecule/primer complex in the presence of a polymerase. Total internal reflectance fluorescence microscopy is then used to visualize the attached target nucleic acid target molecule/primer complex and/or the incorporated nucleotides with single molecule resolution.

Measured signals can be analyzed manually or by appropriate computer methods to tabulate results. The substrates and reaction conditions can include appropriate controls for verifying the integrity of hybridization and extension conditions, and for providing standard curves for quantification, if desired. For example, a control nucleic acid can be added to the sample. The absence of the expected extension product is an indication that there is a defect with the sample or assay components requiring correction.

Fluorescence resonance energy transfer (FRET) can be used as a detection scheme. FRET in the context of sequencing is described generally in Braslavasky, et al., Proc. Nat'l Acad. Sci., 100: 3960-3964 (2003), incorporated by reference herein. Essentially, in one embodiment, a donor fluorophore is attached to the primer, polymerase, or template. Nucleotides added for incorporation into the primer comprise an acceptor fluorophore that is activated by the donor when the two are in proximity.

As described herein, combination articles of manufacture are provided that are suitable for performing the method of the invention. Suitable surfaces are described above. The enzyme can be a ligase or a polymerase, as described above.

The adaptor sequence can optionally comprise a linker moiety at the 5' terminus of the adaptor sequence, the linker moiety being suitable for attaching a target molecule to the surface. Other suitable linker moieties are described above.

EXAMPLE

The 7249 nucleotide genome of the bacteriophage M13mp18 was sequenced using a single molecule system of the invention. Purified, single-stranded viral M13mp18 genomic DNA was obtained from New England Biolabs. Approximately 25 ug of M13 DNA was digested to an average fragment size of 40 bp with 0.1 U Dnase I (New England Biolabs) for 10 minutes at 37° C. Digested DNA fragment sizes were estimated by running an aliquot of the digestion mixture on a precast denaturing (TBE-Urea) 10% polyacrylamide gel (Novagen) and staining with SYBR Gold (Invitrogen/Molecular Probes). The DNase I-digested genomic DNA was filtered through a YM10 ultrafiltration spin column (Millipore) to remove small digestion products less than about 30 nt. Approximately 20 pmol of the filtered DNase I digest was then polyadenylated with terminal transferase according to known methods (Roychoudhury, R and Wu, R. 1980, Terminal transferase-catalyzed addition of nucleotides to the 3' termini of DNA. Methods Enzymol. 65(1):43-62.). The average dA tail length was 50+/−5 nucleotides. Terminal transferase was then used to label the fragments with Cy3-dUTP. Fragments were then terminated with dideoxyTTP (also added using terminal transferase). The resulting fragments were again filtered with a YM10 ultrafiltration spin column to remove free nucleotides and stored in ddH2O at −20° C.

Epoxide-coated glass slides were prepared for oligo attachment. Epoxide-functionalized 40 mm diameter #1.5 glass cover slips (slides) were obtained from Erie Scientific (Salem, N.H.). The slides were preconditioned by soaking in 3×SSC for 15 minutes at 37° C. Next, a 500 pM aliquot of 5' aminated polydT(50) (polythymidine of 50 bp in length with a 5' terminal amine) was incubated with each slide for 30 minutes at room temperature in a volume of 80 ml. The resulting slides had poly(dT50) primer attached by direct amine linkage to the epoxide. The slides were then treated with phosphate (1M) for 4 hours at room temperature in order to passivate the surface. Slides were then stored in polymerase rinse buffer (20 mM Tris, 100 mM NaCl, 0.001% Triton X-100, pH 8.0) until they were used for sequencing.

For sequencing, the slides were placed in a modified FCS2 flow cell (Bioptechs, Butler, Pa.) using a 50 um thick gasket. The flow cell was placed on a movable stage that is part of a high-efficiency fluorescence imaging system built around a Nikon TE-2000 inverted microscope equipped with a total internal reflection (TIR) objective. The slide was then rinsed with HEPES buffer with 100 mM NaCl and equilibrated to a temperature of 50° C. An aliquot of the M13 template fragments described above was diluted in 3×SSC to a final concentration of 1.2 nM. A 100 ul aliquot was placed in the flow cell and incubated on the slide for 15 minutes. After incubation, the flow cell was rinsed with 1×SSC/HEPES/0.1% SDS followed by HEPES/NaCl. A passive vacuum apparatus was used to pull fluid across the flow cell. The resulting slide contained M13 template/oligo(dT) primer duplex. The temperature of the flow cell was then reduced to 37° C. for sequencing and the objective was brought into contact with the flow cell.

For sequencing, cytosine triphosphate, guanidine triphosphate, adenine triphosphate, and uracil triphosphate, each having a cyanine-5 label (at the 7-deaza position for ATP and GTP and at the C5 position for CTP and UTP (PerkinElmer)) were stored separately in buffer containing 20 mM Tris-HCl, pH 8.8, 10 mM MgSO$_4$, 10 mM (NH$_4$)$_2$SO$_4$, 10 mM HCl, and 0.1% Triton X-100, and 100 U Klenow exo$^-$ polymerase (NEN). Sequencing proceeded as follows.

First, initial imaging was used to determine the positions of duplex on the epoxide surface. The Cy3 label attached to the M13 templates was imaged by excitation using a laser tuned to 532 nm radiation (Verdi V-2 Laser, Coherent, Inc., Santa Clara, Calif.) in order to establish duplex position. For each slide only single fluorescent molecules were imaged in this step were counted. Imaging of incorporated nucleotides as described below was accomplished by excitation of a cyanine-5 dye using a 635 nm radiation laser (Coherent). 5 uM Cy5CTP was placed into the flow cell and exposed to the slide for 2 minutes. After incubation, the slide was rinsed in 1×SSC/15 mM HEPES/0.1% SDS/pH 7.0 ("SSC/HEPES/SDS") (15 times in 60 ul volumes each, followed by 150 mM HEPES/150 mM NaCl/pH 7.0 ("HEPES/NaCl") (10 times at 60 ul volumes). An oxygen scavenger containing 30% acetonitrile and scavenger buffer (134 ul HEPES/NaCl, 24 ul 100 mM Trolox in MES, pH 6.1, 10 ul DABCO in MES, pH6.1, 8 ul 2M glucose, 20 ul NaI (50 mM stock in water), and 4 ul glucose oxidase) was next added. The slide was then imaged (500 frames) for 0.2 seconds using an Inova301K laser (Coherent) at 647 nm, followed by green imaging with a Verdi V-2 laser (Coherent) at 532 nm for 2 seconds to confirm duplex position. The positions having detectable fluorescence were recorded. After imaging, the flow cell was rinsed 5 times each with SSC/HEPES/SDS (60 ul) and HEPES/NaCl (60 ul). Next, the cyanine-5 label was cleaved off incorporated CTP by introduction into the flow cell of 50 mM TCEP for 5 minutes, after which the flow cell was rinsed 5 times each with SSC/HEPES/SDS (60 ul) and HEPES/NaCl (60 ul). The remaining nucleotide was capped with 50 mM iodoacetamide for 5 minutes followed by rinsing 5 times each with SSC/HEPES/SDS (60 ul) and HEPES/NaCl (60 ul). The scavenger was applied again in the manner described above, and the slide was again imaged to determine the effectiveness of the cleave/cap steps and to identify non-incorporated fluorescent objects.

The procedure described above was then conducted 100 nM Cy5dATP, followed by 100 nM Cy5dGTP, and finally 500 nM Cy5dUTP. The procedure (expose to nucleotide, polymerase, rinse, scavenger, image, rinse, cleave, rinse, cap, rinse, scavenger, final image) was repeated exactly as described for ATP, GTP, and UTP except that Cy5dUTP was incubated for 5 minutes instead of 2 minutes. Uridine was used instead of thymidine due to the fact that the Cy5 label was incorporated at the position normally occupied by the methyl group in Thymidine triphosphate, thus turning the dTTP into dUTP. In all 64 cycles (C, A, G, U) were conducted as described in this and the preceding paragraph.

Once 64 cycles were completed, the image stack data (i.e., the single molecule sequences obtained from the various surface-bound duplex) were aligned to the M13 reference sequence. The image data obtained was compressed to collapse homopolymeric regions. Thus, the sequence "TCAAAGC" would be represented as "TCAGC" in the data tags used for alignment. Similarly, homopolymeric regions in the reference sequence were collapsed for alignment. The sequencing protocol described above resulted in an aligned M13 sequence with an accuracy of between 98.8% and 99.96% (depending on depth of coverage). The individual single molecule sequence read lengths obtained ranged from 2 to 33 consecutive nucleotides with about 12.6 consecutive nucleotides being the average length.

The alignment algorithm matched sequences obtained as described above with the actual M13 linear sequence. Placement of obtained sequence on M13 was based upon the best match between the obtained sequence and a portion of M13 of the same length, taking into consideration 0, 1, or 2 possible errors. All obtained 9-mers with 0 errors (meaning that they exactly matched a 9-mer in the M13 reference sequence) were first aligned with M13. Then 10-, 11-, and 12-mers with 0 or 1 error were aligned. Finally, all 13-mers or greater with 0, 1, or 2 errors were aligned. At a coverage depth of greater than or equal to 1, 5,001 bases of the 5,066 base M13 collapsed genome were covered at an accuracy of 98.8%. Similarly, at a coverage depth of greater than or equal to 5, 83.6% of the genome was covered at an accuracy of 99.3%, and at a depth of greater than or equal to 10, 51.9% of the genome was covered at an accuracy of 99.96%. The average coverage depth was 12.6 nucleotides.

I claim:

1. A method for obtaining sequence information from a nucleic acid, the method comprising the steps of:
    capturing target nucleic acids with a sequence-specific capture probe to produce a target/probe duplex;
    melting said target/probe duplex to release said target nucleic acids;
    annealing a primer to the target nucleic acids to produce a target/primer duplex;
    attaching said target/primer duplex to a surface such that at least a portion of said target/primer duplex is individually optically resolvable;
    introducing a polymerase and at least one nucleotide species comprising an optically-detectable label under conditions sufficient for template-dependent nucleotide addition;
    removing unincorporated nucleotide; and
    identifying nucleotide species incorporated into the extended primer, thereby obtaining sequence information from said target.

2. The method of claim 1, further comprising the step of removing said optically-detectable label from nucleotide incorporated into said primer.

3. The method of claim 1, wherein said capturing step comprises hybridizing said target nucleic acids to capture probes immobilized in a polyacrylamide gel.

4. The method of claim 1, wherein said capture probes are attached to a bead.

5. The method of claim 1, wherein said optically-detectable label is a fluorescent label.

6. The method of claim 1, wherein said introducing, removing, and identifying steps are repeated at least once.

7. The method of claim 1, wherein said surface comprises an epoxide.

8. The method of claim 1, wherein said attaching step comprises modifying said target nucleic acid to introduce a 3' or 5' amine.

9. The method of claim 1, wherein said surface is streptavidnated.

10. The method of claim 9, wherein said target and/or said primer comprise a biotin end label.

11. The method of claim 1, wherein the sequence specific-capture probes of multiple sequences are used.

12. The method of claim 1, wherein the target nucleic acids are produced as a result of fragmentation by sonication.

* * * * *